(12) United States Patent
Okuda et al.

(10) Patent No.: US 7,968,832 B2
(45) Date of Patent: Jun. 28, 2011

(54) ANALYZER AND USE THEREOF

(75) Inventors: Yohei Okuda, Tsuruga (JP); Keizo Yoneda, Tsuruga (JP)

(73) Assignee: Toyo Boseki Kabushiki Kaisha, Osaka-shi (JP)

( * ) Notice: Subject to any disclaimer, the term of this patent is extended or adjusted under 35 U.S.C. 154(b) by 374 days.

(21) Appl. No.: 12/307,640

(22) PCT Filed: Jul. 12, 2007

(86) PCT No.: PCT/JP2007/063878
§ 371 (c)(1),
(2), (4) Date: Jan. 6, 2009

(87) PCT Pub. No.: WO2008/007725
PCT Pub. Date: Jan. 17, 2008

(65) Prior Publication Data
US 2009/0206234 A1 Aug. 20, 2009

(30) Foreign Application Priority Data

Jul. 12, 2006 (JP) .................................. 2006-191807

(51) Int. Cl.
*G02B 21/00* (2006.01)
(52) U.S. Cl. ..................................... 250/201.3; 359/383
(58) Field of Classification Search .... 250/201.2–201.4; 382/128, 133; 359/383
See application file for complete search history.

(56) References Cited

U.S. PATENT DOCUMENTS

| | | | |
|---|---|---|---|
| 4,342,905 A | 8/1982 | Fujii et al. | |
| 5,989,835 A * | 11/1999 | Dunlay et al. | 506/10 |
| 6,151,405 A | 11/2000 | Douglass et al. | |
| 6,215,892 B1 | 4/2001 | Douglass et al. | |
| 6,285,498 B1 * | 9/2001 | Mayer | 359/392 |
| 6,330,349 B1 | 12/2001 | Hays et al. | |

(Continued)

FOREIGN PATENT DOCUMENTS

JP 10-111445 A 4/1998

(Continued)

OTHER PUBLICATIONS

*Atlas of Clinical Laboratory Examination 1, Urinary Sediment* (Kiyoshi Okuda, ed.), pp. 24-29 (Ishiyaku Publishers, Inc., Tokyo, 1981).

(Continued)

*Primary Examiner* — Tony Ko
(74) *Attorney, Agent, or Firm* — Leydig, Voit & Mayer, Ltd.

(57) ABSTRACT

This invention provides an analyzer for judging whether or not a tangible component is present in a sample in a preparation, and analyzing, if a tangible component is present, the tangible component with efficiency and high accuracy. For this purpose, an analyzer (100) of the present invention analyzes a tangible component in a sample (23) held by a preparation (20). The analyzer (100) checks whether or not a tangible component is present in the sample (23) by extensively observing an area in a certain visual field in which area the tangible component is assumed to be present. If the tangible component is judged to be present, the analyzer (100) analyzes the tangible component. Then, another visual field is selected, and another analysis is started therein so as to analyze only in the vicinity of the area where the tangible component was judged to be present. The analyzer (100) can determine whether or not a tangible component is present, and can analyze the tangible component with efficiency and high accuracy.

11 Claims, 12 Drawing Sheets

U.S. PATENT DOCUMENTS

| | | |
|---|---|---|
| 6,348,325 B1 | 2/2002 | Zahniser et al. |
| 6,418,236 B1 | 7/2002 | Ellis et al. |
| 6,458,601 B1 | 10/2002 | Kimura |
| 6,546,123 B1 | 4/2003 | McLaren et al. |
| 6,553,135 B1 | 4/2003 | Douglass et al. |
| 6,661,501 B1 | 12/2003 | Zahniser et al. |
| 6,665,060 B1 | 12/2003 | Zahniser et al. |
| 6,718,053 B1 | 4/2004 | Ellis et al. |
| 6,980,293 B1 | 12/2005 | Harada |
| 7,006,674 B1 | 2/2006 | Zahniser et al. |
| 7,345,814 B2 | 3/2008 | Yoneyama et al. |
| 2001/0024834 A1 | 9/2001 | Kimura |
| 2001/0033414 A1 | 10/2001 | Yahiro |
| 2002/0076092 A1 | 6/2002 | Ellis et al. |
| 2002/0150967 A1 | 10/2002 | Zahniser et al. |
| 2002/0176613 A1 | 11/2002 | Hays et al. |
| 2002/0186874 A1 | 12/2002 | Price et al. |
| 2003/0179445 A1 | 9/2003 | Maenle et al. |
| 2003/0228038 A1 | 12/2003 | Douglass et al. |
| 2004/0058401 A1 | 3/2004 | Bossy et al. |
| 2004/0066960 A1 | 4/2004 | McLaren et al. |
| 2004/0071327 A1 | 4/2004 | Ellis et al. |
| 2004/0105000 A1 | 6/2004 | Yuri |
| 2004/0120562 A1 | 6/2004 | Hays et al. |
| 2004/0132197 A1 | 7/2004 | Zahniser et al. |
| 2004/0136581 A1 | 7/2004 | Ellis et al. |
| 2005/0068614 A1 | 3/2005 | Yoneyama et al. |
| 2005/0118640 A1 | 6/2005 | Kureshy et al. |
| 2005/0124059 A1 | 6/2005 | Kureshy et al. |
| 2005/0170356 A1 | 8/2005 | Kureshy et al. |
| 2005/0179899 A1* | 8/2005 | Palti-Wasserman et al. . 356/417 |
| 2005/0185832 A1 | 8/2005 | Douglass et al. |
| 2005/0196325 A1 | 9/2005 | Bathe et al. |
| 2005/0233325 A1 | 10/2005 | Kureshy et al. |
| 2005/0233437 A1 | 10/2005 | Kureshy et al. |
| 2006/0077538 A1 | 4/2006 | Zahniser et al. |
| 2006/0077541 A1 | 4/2006 | Zahniser et al. |
| 2006/0104499 A1 | 5/2006 | Zahniser et al. |
| 2007/0053569 A1 | 3/2007 | Douglass et al. |
| 2007/0140540 A1 | 6/2007 | McLaren et al. |
| 2007/0206843 A1 | 9/2007 | Douglass et al. |
| 2008/0013168 A1 | 1/2008 | Maenle et al. |
| 2008/0013812 A1 | 1/2008 | Maenle et al. |
| 2008/0018994 A1 | 1/2008 | Maenle et al. |
| 2008/0123185 A1 | 5/2008 | Yoneyama et al. |
| 2008/0204865 A1 | 8/2008 | Yoneyama et al. |
| 2008/0258061 A1 | 10/2008 | Douglass et al. |
| 2008/0260233 A1 | 10/2008 | Hays et al. |

FOREIGN PATENT DOCUMENTS

| | | |
|---|---|---|
| JP | 10-185803 A | 7/1998 |
| JP | 11-095091 A | 4/1999 |
| JP | 2000-035384 A | 2/2000 |
| JP | 2001-027729 A | 1/2001 |
| JP | 2001-255260 A | 9/2001 |
| JP | 2002-014100 A | 1/2002 |
| JP | 2004-340759 A | 12/2004 |
| JP | 2005-128493 A | 5/2005 |
| JP | 2006-029824 A | 2/2006 |

OTHER PUBLICATIONS

*Outline of Clinical Laboratory Examination Methods* (Masamitsu Kanai, ed.), pp. 298-299 (Kanehara & Co., Ltd., Tokyo, 2005).

*All About Staining Methods* (Monthly Medical Technology, ed.), pp. 16-25, 38-39, 114-121, 130-131, 140-143, 152-157, and 200-207 (Ishiyaku Publishers, Inc., Tokyo, 1986).

*Complete Book of Techniques of Clinical Laboratory Examination*, vol. 3: Blood Test, pp. 132-135 (Igaku-Shoin Ltd., Tokyo, 1982).

* cited by examiner $Y = 0.95X + 15.2$
$r = 0.9923$

ANALYZER AND USE THEREOF

TECHNICAL FIELD

The present invention relates to: an analyzer for analyzing a tangible component in a sample; and a use thereof, and especially relates to: the analyzer capable of carrying out, with high efficiency and high accuracy, an analysis of a tangible component in various kinds and types of biological samples by using a unique automatic focusing function; and a use thereof.

BACKGROUND ART

An analysis of a tangible component in a biological sample in the medical field requires a classification of various kinds and types of tangible components. Therefore, there has been a problem such as that: (i) it takes a long time to train an expert medical technologist; (ii) it is necessary to observe a tangible component by using a microscope for a long time; and (iii) a result of an analysis varies greatly between individuals and facilities. Examples of such the analysis of the tangible component in the biological sample encompass an analysis of a urinary sediment component. The analysis of the urinary sediment component is constituted by a plurality of steps such as: (i) subjecting a urinary sample to centrifugation so as to separate the urinary sample into a sediment component and a supernatant component; (ii) removing the supernatant component; (iii) taking out a part of the sediment component, smearing the part of the sediment component onto a slide glass, and sealing the slide glass with a cover glass, so as to prepare a preparation; and (iv) analyzing the preparation by using an optical microscope. Generally, these steps are carried out manually by a person. Therefore, these steps put a heavy burden to a medical technologist. Further, there is a problem in accuracy in an analysis and a judgment because the result obtained by the analysis and the judgment varies greatly between medical technologists.

In order to solve the foregoing problems, an analyzer for analyzing a tangible component in a biological sample in an automated manner was developed recently. Such an analyzer is getting more and more used in the clinical field. For example, Patent Document 1 discloses a urinary tangible component classification device including means for (i) automatically focusing on a tangible component in liquid to be examined (particularly, urine) and (ii) taking an image of the liquid to be examined (urine) placed on a light-transmitting plate or contained in a flow cell, for the purpose of minutely and accurately classifying the tangible component in the urine. Further, in the urinary tangible component classification device, the means is provided with an automatic focusing function for automatically focusing on a tangible component in liquid to be examined.

Further, for example, Patent Document 2 discloses a microscope system for setting in advance, as a focus point, a position which is at a predetermined distance from a starting point set at a bottom surface of a container, for the purpose of observing a cell attachment, although an objective of this technique is not to analyze a tangible component in a biological sample.

Furthermore, as another automatic focusing technique, Patent Document 3 provides such a method that (i) a position where an object to be observed is assumed to be present is set in advance, (ii) a focusing operation is carried out at the position thus set, and (iii) if a focus state is not obtained, the focusing operation is carried out finely around the set value until the focus state is obtained.

The analyzer disclosed in Patent Document 1, however, analyzes a tangible component in a biological sample by using a Flow cytometer, and does not prepare a sample (e.g., a preparation) on which an object to be examined is applied. Therefore, without any modifications, the analyzer cannot be used as a device for carrying out an analysis by preparing a sample (e.g., a preparation) on which an object to be examined is applied.

A tangible component in a biological sample is not fixed in a preparation, but is flowing in the preparation. Because the technique disclosed in Patent Document 2 is for observing a sample fixed in a preparation, the technique is not suitable for an analysis of a sample which is flowing in a preparation. Further, in a biological sample, there are various kinds of tangible components having different shapes and colors. Therefore, the tangible components do not have a certain focus position which is fixed. For this reason also, it is impossible to use the technique disclosed in Patent Document 2 for analyzing a tangible component in a biological sample.

The technique disclosed in Patent Document 3 is established on the premise that a cell to be observed is present in a sample. However, in an analysis of a tangible component in a biological sample, it is unknown whether or not the tangible component is present in the biological sample. For this reason, it is also impossible to use the technique disclosed in Patent Document 3 for the purpose of analyzing a tangible component in a biological sample.

As well as an analysis of a tangible component in a biological sample, an analysis of a tangible component in a non-biological sample (such as a sample for a water quality test) has the foregoing problems.

Therefore, there has been a strong demand for development of an analyzer available for both biological sample and non-biological sample, which analyzer (i) judges whether or not a tangible component is present in a sample in a preparation and (ii) if the tangible component is present, analyzes the tangible component with efficiency and high accuracy.

[Patent Document 1]
Japanese Unexamined Patent Application Publication, Tokukai, No. 2001-255260 (published on Sep. 21, 2001)

[Patent Document 2]
Japanese Unexamined Patent Application Publication, Tokukai, No. 2001-296478 (published on Oct. 26, 2001)

[Patent Document 3]
Japanese Unexamined Patent Application Publication, Tokukaihei, No. 11-95091 (published on Apr. 9, 1999)

DISCLOSURE OF INVENTION

The present invention was made in view of the foregoing problems, and an objective of the present invention is to provide: (i) an analyzer for (a) judging whether or not a tangible component is present in a sample in a preparation and (b) if the tangible component is judged to be present, carrying out an analysis of the tangible component with efficiency and high accuracy; and (ii) a use of the analyzer.

In view of the foregoing problems, the diligent work of the inventors of the present invention has reached the following finding: In a case where (i) it is checked whether or not a tangible component is present in a certain visual field by extensively observing an area in the certain visual field in which area a tangible component to be analyzed is assumed to be present, (ii) if it is judged that the tangible component is present in the certain visual field, an analysis of the tangible component is carried out, (iii) and then, another visual field is selected so that another analysis is started therein, observing only in the vicinity of the area where the tangible component has been judged to be present allows (a) to judge whether or not a tangible component is present in said another visual field, (b) to carry out, with high accuracy, an analysis of the tangible component which is judged to be present, and (c) to carry out an analysis of other tangible components efficiently. With this finding, the inventors have completed the present invention.

Further, the inventors have found a problem caused by a manufacturing allowance of a light-transmitting plate and a light-transmitting covering plate included in a preparation. The problem is caused as follows: (i) The manufacturing allowance causes differences in thickness of light-transmitting plates and light-transmitting covering plates, (ii) such the difference in thickness slightly varies a distance between an objective lens and a tangible component in the preparation, that is, a depth of a focus point, and (iii) this causes a difference in focus point between the preparations, thereby making it difficult to automatically and accurately focus on each of the preparations. In view of this problem, the inventors have found that: the effect caused by the difference in thickness between the preparations is eliminated by a process for (i) carrying out focusing operation for each preparation and (ii) determining an analysis start position in accordance with a focus position obtained as a result of the focusing operation; and this makes it possible to quickly and accurately carry out automatic focusing operation with respect to a tangible component in a biological sample so that an analysis of the tangible component is carried out. With this finding, the inventors have completed the present invention.

That is, an analyzer according to the present invention is for analyzing a tangible component contained in a sample held between a light-transmitting plate and a light-transmitting covering plate, the analyzer including: an objective lens for observing the sample; focus state detecting means for detecting a focus state of the objective lens; drive means for changing, in three dimensional directions, a relative position between the objective lens and the sample; automatic focusing means for controlling the drive means in accordance with a detection result obtained by the focus state detecting means, so as to perform automatic focusing operation to automatically focus the objective lens; control means for controlling the automatic focusing means and/or the drive means so as to carry out the automatic focusing operation in a range from a predetermined analysis start position to a preset analysis end position, the predetermined analysis start position being between the light-transmitting plate and the light-transmitting covering plate; and judgment means for judging that, when the focus state detecting means detects the focus state in the automatic focusing operation, the tangible component is present in a focus position at which the focus state is obtained. Further, if the judgment means judges that the tangible component is present, the control means controls the automatic focusing means and/or the drive means so as to stop the automatic focusing operation at the focus position at which the tangible component is judged to be present, and changes, in a horizontal direction, the relative position between the objective lens and the sample so that another analysis of a tangible component is carried out in another visual field. Furthermore, in a case where said another analysis of the tangible component is carried out in said another visual field, the control means carries out the automatic focusing operation in a predetermined distance in the vicinity of the focus position at which, in the analysis carried out before said another analysis, the tangible component is judged to be present, the predetermined distance being in a vertical direction (i.e., a direction elongating from the light-transmitting plate to the light-transmitting covering plate).

With this arrangement, firstly, it is confirmed whether or not the tangible component is present in a desired visual field by extensively observing an area in the desired visual field in which area the tangible component to be analyzed is assumed to be present. If it is judged that the tangible component is present therein, the analysis of the tangible component is carried out. Then, another visual field is selected so that another analysis is started therein. At this time, said another analysis is carried out in the vicinity of the area where the tangible component has been judged to be present.

This operation allows a highly-accurate judgment of whether or not a tangible component is present. Further, the inventors have originally found such a knowledge that if a tangible component is judged to be present in a certain visual field, there is a high possibility that a tangible component is also present at the same position (the same height) in other visual fields. Based on this knowledge, the analyzer of the present invention may be arranged such that, for example, in a case where an analysis is carried out in a plurality of visual fields, an analysis in a subsequent visual field(s) following a preceding visual field is carried out only in the vicinity of an area where a tangible component has been judged to be present in the analysis in the preceding visual field. Thus, with the analyzer of the present invention, in the case where an analysis is carried out in a plurality of visual fields, it is not necessary to repeatedly carry out analysis operation with an initial setting (i.e., operation for extensively observing an area where a tangible component is assumed to be present) in all of the visual fields. This reduces time taken for an analysis, thereby allowing to carry out the analysis efficiently.

Thus, with the analyzer according to the present invention, it is possible to judge whether or not a tangible component is present in a sample in a preparation. Further, if the tangible component is judged to be present, it is possible to carry out an analysis of the tangible component with efficiency and high accuracy.

An analysis method according to the present invention includes the steps of: carrying out automatic focusing operation in a range from a predetermined analysis start position to a preset analysis end position, the predetermined analysis start position being between the light-transmitting plate and the light-transmitting covering plate; judging whether or not a tangible component is present, wherein if a focus state is detected in the step for carrying out the automatic focusing operation, it is judged that a tangible component is present in a focus position at which the focus state is obtained; if it is judged that the tangible component is present in the judgment step, stopping the automatic focusing operation at the focus position at which the tangible component is judged to be present, and changing, in a horizontal direction, a relative position between the objective lens and the sample so as to carry out another analysis of a tangible component in another visual field; and carrying out, in said another analysis of the tangible component in said another visual field, the automatic focusing operation in a predetermined distance in the vicinity of the focus position at which the tangible component is judged to be present, the predetermined distance being in a vertical direction.

With this, it is possible to judges whether or not the tangible component is present in the sample in the preparation. Further, if the tangible component is judged to be present, it is possible to carry out an analysis of the tangible component with efficiency and high accuracy.

Additional objects, features, and strengths of the present invention will be made clear by the description below. Further, the advantages of the present invention will be evident from the following explanation in reference to the drawings.

BRIEF DESCRIPTION OF DRAWINGS

FIG. 6 (b) is a perspective view of a slide glass 31 integrating a cover glass.

BEST MODE FOR CARRYING OUT THE INVENTION

First Embodiment

Figure 1:
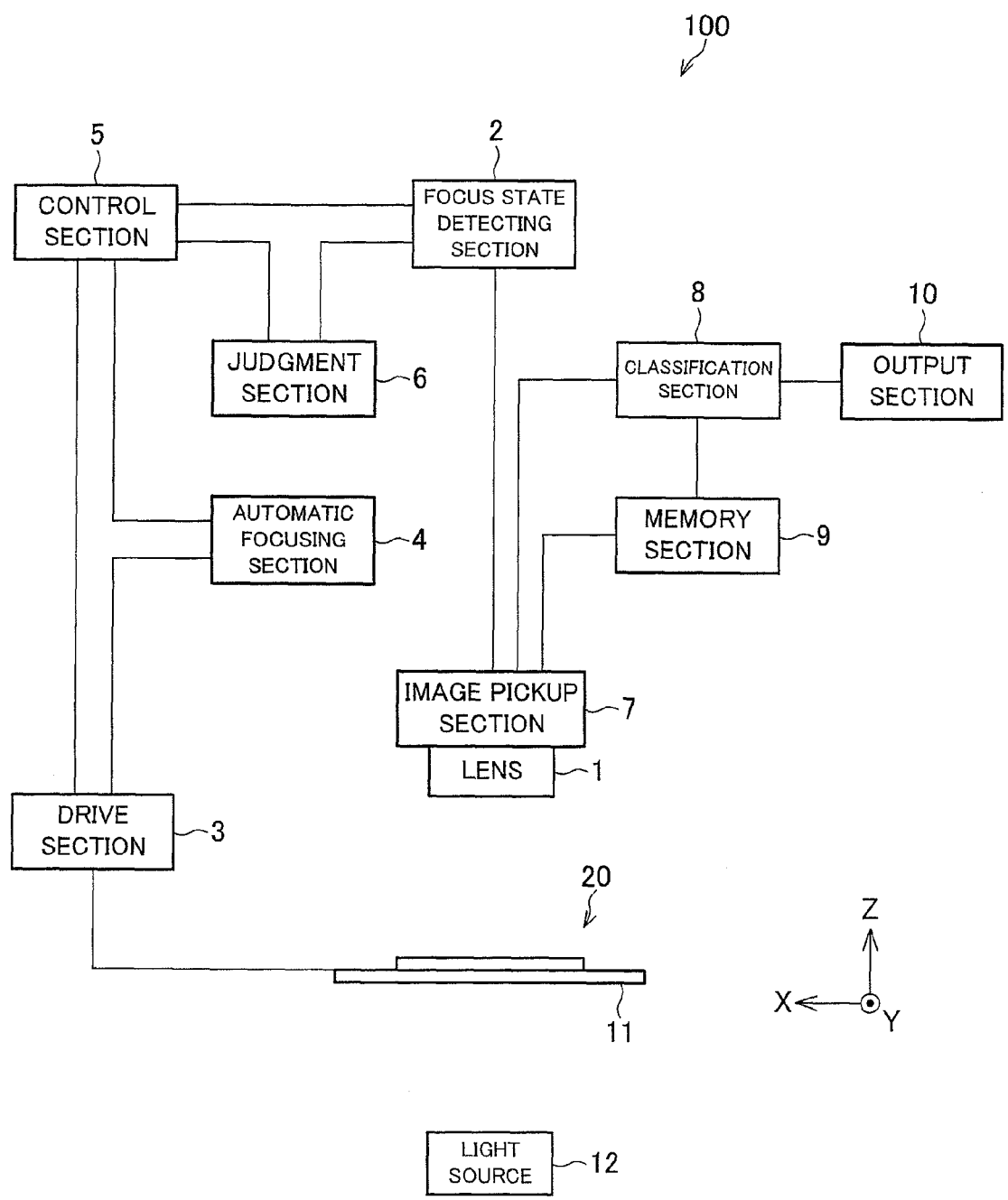
FIG. 1 is a schematic view of an arrangement of an analyzer according to one embodiment of the present invention.

The following describes one embodiment of the present invention. Note that the present invention is not limited to the embodiment described below.

An analyzer according to the present invention is an analyzer for carrying out an analysis of a tangible component contained in a sample held between a slide glass (a light-transmitting plate) and a cover glass (a light-transmitting covering plate). Further, the analyzer automatically focuses on a tangible component in a sample quickly and accurately by using a unique control mechanism, thereby allowing an efficient and accurate analysis, the analysis including a judgment of whether or not a tangible component is present. Furthermore, the analyzer eliminates an effect caused by a difference in thickness between preparations, and is capable of carrying out an analysis with high accuracy.

The "sample" in the present specification may be any sample that can include a tangible component and is desired to be examined. Examples of the sample may encompass: a biological sample obtained by a living thing; and a non-biological sample. The biological sample is not particularly limited, but may be: the whole component of a blood; spinal fluid; prostatic fluid; urine; ascites; synovial fluid; tear; saliva; serum; blood plasma; or the like. The biological sample may preferably be urine, for example, in a form of raw urine, concentrated urine, and a urinary sediment resulting from centrifugation of urine. The non-biological sample may be other fluid samples having non-biological characteristics. Examples of the non-biological sample may encompass a sample for a water quality test or for an environmental survey.

Further, the "tangible component" only needs to be a solid tangible component included in a sample. Except for this point, a specific arrangement of the "tangible component" is not particularly limited. For example, a tangible component in a biological sample only needs to be the one which is dispersed or suspended in the biological sample. For example, in a case where urine is used as a biological sample, the tangible component may be: red blood cells such as a normal red blood cell and a deformed red blood cell; white blood cells such as a pale cell, a dark cell, and a glitter cell; epithelia such as a flat epithelium, a transitional epithelium, a tubular epithelium, and a columnar epithelium; casts such as a hyaline cast, a granular cast, a waxy cast, an epithelial cast, a red blood cell cast, a white blood cell cast, a fatty cast, a vacuolar-denatured cast, a hemoglobin cast, a hemosiderin cast, a myoglobin cast, a bilirubin cast, an amyloid cast, a Bence-Jones cast, a platelet cast, a bacterial cast, a salt cast, a crystalline cast, and a wide cast; micro organisms such as a coccus, a bacillus, a fungus, and a yeast fungus; parasites such as a trichomonad, a malaria parasite, and a mite; crystals such as a calcium oxalate crystal, a uric acid crystal, a urate, a uroammoniac crystal, a calcium phosphate crystal, a magnesium ammonium phosphate crystal, a bilirubin crystal, a tyrosine crystal, a leucine crystal, a cystine crystal, a cholesterol crystal, a 2.8-dihydroxyadenine (DHA) crystal, a calcium carbonate crystal, and an exogenous crystal; amorphous salts such as an amorphous urate and an amorphous phosphate; an oval fat body; a fat globule; an intracytoplasmic inclusion; an intranuclear inclusion; a sperm; a macrophage; or the like.

Furthermore, by the description "held between a slide glass and a cover glass", a sample (such as a preparation) on which an object to be examined is applied is intended. The sample is not particularly limited, but may be a sample to be examined which is prepared by using a conventional preparation known to public.

The "analysis (analyzing)" in the present specification means one of or a combination of a plurality of conventional analysis methods known to public, such as an observation, a judgment, a classification, a comparison, a gauging, a measurement, and an assay, each of which is of a tangible component.

Figure 2:
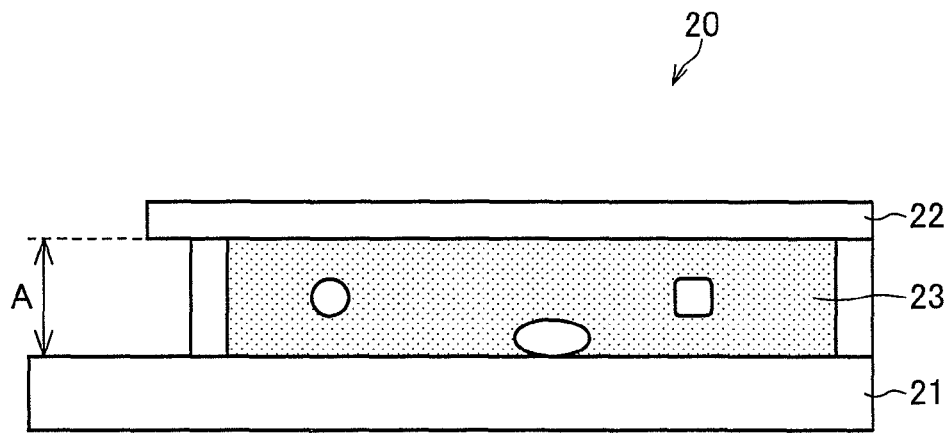
FIG. 2 is a schematic view of an arrangement of a preparation used in the analyzer according to one embodiment of the present invention.

The following describes, with reference to drawings, one embodiment of an analyzer according to the present invention in detail. FIG. 1 is a schematic view of an arrangement of an analyzer according to one embodiment of the present invention. As shown in FIG. 1, an analyzer 100 includes an objective lens 1, a focus state detecting section 2, a drive section 3, an automatic focusing section 4, a control section 5, a judgment section 6, an image pickup section 7, a classification section 8, a memory section 9, an output section 10, a stage 11, and a light source 12. A preparation 20 is placed on the stage 11. As shown in FIG. 2, the preparation 20 includes a slide glass (a light-transmitting plate) 21 and a cover glass (a light-transmitting covering plate) 22. Further, a sample 23 is held between the slide glass 21 and the cover glass 22.

An arrangement of the objective lens 1 is not particularly limited. The objective lens 1 only needs to be capable of observing the sample 23 placed on the stage 11, and may use a conventional lens known to public.

The focus state detecting section 2 functions as focus state detecting means for detecting a focus state of the objective lens 1, particularly, a focus state with respect to the sample 23. The means for detecting the focus state is not particularly limited, but may be a conventional focus state detecting method known to public. For example, the focus state detecting section 2 may be arranged so as to: (i) determine, as an evaluation value, variance of a luminance level obtained in automatic focusing operation; (ii) detect a timing at which the evaluation value obtains a minimum value; and (iii) determine that a position of the objective lens 1 at the timing is a position in a focus state. The method for detecting the focus state will also be described later in detail, in a description regarding the automatic focusing section 4.

The drive section 3 functions as drive means for changing, in three dimensional directions, a relative position between the objective lens 1 and the sample 23. In other words, the drive section 3 functions as drive means for changing, in three dimensional directions, the relative position between the objective lens 1 and the stage 11. As the drive section 3, a conventional drive means known to public may preferably be used. For example, the drive section 3 may be the one which allows mechanical driving (e.g., a servo motor, a stepping motor, and a linear motor).

Further, in the present embodiment, the drive section 3 is arranged so as to move the stage 11 for the purpose of changing the relative position between the objective lens 1 and the sample 23. However, the present invention is not limited to this. For example, the drive section 3 may be arranged so as to drive the objective lens 1 or to drive both of the objective lens 1 and the stage 11. Particularly, it is preferable to arrange the drive section 3 so that the drive section 3 drives the stage 11, in view of (i) simplicity of an arrangement and (ii) stability in driving.

In the present specification, for convenience of description, as shown in FIG. 1, a vertical direction elongating from the objective lens 1 to the sample 23 is denoted as a z-axis direction, and horizontal directions parallel to the preparation 20 are denoted as an x-axis direction and a y-axis direction, respectively.

The automatic focusing section 4 functions as automatic focusing means for controlling the drive section 3 in accordance with a detection result transmitted from the focus state detecting section 2 so as to automatically focus the objective lens 1. A method of the automatic focusing operation carried out by the automatic focusing section 4 may be a conventional automatic focusing method known to public, and its specific arrangement is not particularly limited. Examples of the method encompass an active automatic focusing method and a passive automatic focusing method. Of these, the passive automatic focusing method is preferable.

In a case of using the passive automatic focusing method, a method for detecting the focus state may be, specifically, (I) a method for detecting a focus point by using a change in an electric signal obtained by conversion of a light intensity of an object whose image is to be taken, (II) a method for detecting a focus point by carrying out a phase difference detection and using a phase difference analysis, (III) a method, using an auxiliary light-emitting device which is provided in addition to a light source, for detecting a focus point in accordance with a distance obtained by conversion of light reflected by an object whose image is to be taken, (IV) or the like. Of these, it is preferable to use the method for detecting the focus point by using the change in the electric signal obtained by the conversion of the light intensity of the object whose image is to be taken. Moreover, it is more preferable to use a so-called contrast-based type. The contrast-based type detects a focus point by (i) recognizing, as a contrast, a light intensity detected by an image pickup element for taking an image of an object whose image is to be taken, and (ii) detecting a high-frequency component of the contrast. That is, it is preferable that the automatic focusing section 4 carries out the automatic focusing operation by using the contrast-based type automatic focusing operation function.

As described above, the method (denoted as (II) in the description above), which uses the phase difference analysis, may be a phase-difference detection method. In the phase-difference detection method, one or a plurality of pair(s) of sensors (e.g., line sensors) for detecting an image to be taken is/are provided in the vicinity of a surface equivalent to an image pickup surface on which an image pickup element such as a silver salt film and a photoelectric conversion element is provided. Then, after light has passed through an objective lens, light fluxes of different parts in the light are directed to different sensors, respectively. After that, in accordance with a difference between the pair of sensors with respect to a position of an object whose image is to be taken, a focus point of the objective lens is detected.

As described above, the method (denoted as (III) in the description above) detects a focus point based on a distance between a camera and an object whose image is to be taken, the distance being obtained by using light reflected from the object whose image is to be taken. The method (III) may be an infrared method. In the infrared method, a device for emitting auxiliary light (e.g., an infrared ray) is provided. Then, triangulation is carried out so as to convert, into a distance, an incidence angle of the infrared ray reflected from an object whose image is to be taken. After that, based on the result of the triangulation thus obtained, an absolute value of the distance between the camera and the object whose image is to be taken is worked out.

That is, the focus state detecting section 2 may be arranged so as to use an appropriate method from among the foregoing focus state detecting methods, in order to suit to an automatic focusing method adopted by the automatic focusing section 4.

Further, in the present embodiment, the automatic focusing section 4 is arranged so as to carry out the automatic focusing operation in the following manner: The drive section 3 is controlled so as to drive the stage 11 and thereby to change, in the z-axis direction, the relative distance between the objective lens 1 and the sample 23. A method for moving the stage 11 may be (I) a continuous moving method or (II) a stepwise moving method in which the stage 11 moves a predetermined distance step by step. The method for moving the stage 11 is not particularly limited to either of the two. Further, a specific procedure in both of the two is not particularly limited, and may use a procedure known to public. For example, the continuous moving method (denoted as (I)) may be a method in which: the stage 11 is moved at every predetermined cycle, the cycle being very short; a focus point state is evaluated at every predetermined cycle; and a position presenting a best focus point state is set as a position in a focus state. On the other hand, the stepwise moving method (denoted as (II)) may be a method in which: offset driving is carried out toward a plurality of preset positions; a focus point state at each of the positions is evaluated; and a position presenting a best focus point state is set as a position in a focus state.

The control section 5 functions as control means for controlling each means in the analyzer 100. For example, the control section 5 functions as control means for controlling the automatic focusing section 4 and/or the driving section 2 so as to carry out the automatic focusing operation in a range from a predetermined analysis start position to a preset analysis end position, the predetermined analysis start position being between the slide glass 21 and the cover glass 22. The "analysis start position" and the "analysis end position" are provided between a slide glass and a cover glass. Further, the "analysis start position" and the "analysis end position" are different from each other in a height position in the vertical direction (i.e., a position on the z-axis), but are the same in a horizontal position (i.e., a position on the x-axis and the y-axis). Specific positions of the analysis start position and the analysis end position are not particularly limited, but may be arbitrarily set by a user, depending on a purpose of examination or an object to be examined. The control operation carried out by the control section 5 will be described in detail later.

The judgment section 6 functions as judgment means for judging whether or not a tangible component is present in the sample 23. For example, the judgment section 6 functions as judgment means for judging, if the focus state detecting section 2 detects a focus state in the automatic focusing operation, that a tangible component is present at a focus position at which the focus state is obtained. The judgment operation carried out by the judgment section 6 will also be described in detail later.

The image pickup section 7 functions as image pickup means for obtaining an image of the sample 23. For example, the image pickup section 7 may preferably be the one which, if the judgment section 6 judges that a tangible component is present in the sample 23, obtains an image of the tangible component at a focus position. Further, the image pickup section 7 may preferably the one which, if the judgment section 6 judges that no tangible component is present in a visual field under operation, obtains an image of the sample at an analysis end position where the automatic focusing operation is ended.

The image pickup section 7 may be conventional image pickup means known to public, and its specific arrangement is not particularly limited. It is preferable that the image pickup section 7 use, for example, image pickup means capable of: converting an image into an electric signal by using a semiconductor element which responds to light; and storing the electric signal as digital data in a storage medium. Examples of the image pickup means 7 may encompass a digital still camera, a digital video camera, a CCD digital camera, and a CMOS digital camera.

The classification section 8 functions as classification means for classifying, in accordance with an image obtained by the image pickup section 7, a tangible component included in the sample 23. In other words, the classification section 8 may function as tangible component classification means for automatically classifying and/or measuring, in accordance with the image obtained by the image pickup section 7, a tangible component contained in the sample 23. Specifically, the classification operation carried out by the classification section 8 may be realized by using a conventional classification method known to public, and is not particularly limited.

For example, the classification section 8 may carry out the classification operation by using a classification program. The classification program classifies a tangible component in accordance with its size, its shape, its color, and/or the like. It is preferable that the classification program is realized by computer software. The classification program may preferably be, for example, the one which carries out a classification by (a) carrying out, with respect to a tangible component whose image has been taken, (i) a color extraction step for separating colors according to brightness and chromaticity based on an RGB value, (ii) an image binarization processing step including spot removal, line segment writing, and image separation, and (iii) a characteristic amount calculation step for working out a characteristic amount such as an area, circularity, a circle-equivalent diameter, a perimeter, an absolute maximum amount, an X/Y ratio in Feret's diameter, an X/Y ratio in maximum chord length, and a ratio between a short axis length and a long axis length and (b) comparing the characteristic amount thus obtained with a preset set value of a tangible component. Further, the classification program may preferably be the one including, in addition to the above-mentioned functions, a learning function for the purpose of carrying out a best classification. Examples of such the classification program may encompass the one disclosed in Patent Document 1.

Examples of the learning function may encompass neural network logic having self-learning ability. For example, it is possible to classify various components by using a Rumelhart type neural network. This type of neural network carries out, in advance, learning by using a large amount of data referring to a judgment made by an expert, and has an optimized coupling coefficient between neurons. Therefore, with this neural network, it is possible to automatically classify a component to be examined, by executing neural network operation with use of a parameter which is inputted.

The memory section 9 functions as memory means for storing various data such as: an image which is taken by the image pickup section 7; the classification program; and a result of an analysis performed by the analyzer 100. The memory section 9 may be a conventional memory or a conventional storage member each of which is known to public, and its specific arrangement is not particularly limited. Further, the memory section 9 may be a built-in type such as hard disk or may be an external type such as an external storage device. That is, examples of the memory section 9 may encompass hard disk, a magneto-optical disk, a DVD, a CD-ROM, a flash memory, and a digital video disk.

The output section 10 is for externally outputting and displaying various information regarding the analyzer 100. For example, the output section 10 may output and display information regarding mechanical operation such as automatic focusing operation. Further, the output section 10 may output and display, in a list or in a combined manner, images which are obtained. In the combined manner, for example, a desired number of the images are overlapped with each other or the images are arranged in matrix. Furthermore, the output section 10 may output/display information regarding additional control with respect to each means and member (e.g., storage of an image or a result of a measurement). Moreover, the output section 10 may output/display a result of an analysis or a classification. In a case where images are to be overlapped, it is preferable that (i) ranges of the images do not overlap each other and (ii) the images are taken in the same magnification scale and the same pixels. The output section 10 may preferably be a conventional display known to public. In a case where a display is used as the output section 10, the output section 10 may be provided with the following functions: a function for displaying, in addition to a measurement result and image data, an item such as time and a current state of the analyzer (e.g., a measurement state with respect to a sample, assumed measurement end time or remaining time required for a measurement each of which time is for samples or a selected sample, the amount of waste liquid in a waste liquid vessel, a remaining amount of purified water in a purified water vessel, a remaining amount of a reagent, and a remaining amount of a cleaning agent), in accordance with a selected menu; and a function for magnifying and displaying information which is selected so that the information can be read from a distance. Further, the output section 10 may be provided with, as needed, conventional printing means known to public and an arrangement (printing means) for outputting necessary information as a hard copy (e.g., paper).

The stage 11 functions as sample supporting means on which the preparation 20 is placed. The stage 11 may preferably be, for example, a sample stage to be used in a conventional microscope known to public or the like, and its specific arrangement is not particularly limited. The stage 11 only needs to (i) be movable in the x-axis and y-axis directions for the purpose of shifting a visual field one from another and (ii) be movable in the z-axis direction for the purpose of adjusting a focus point. That is, the stage 11 only needs to be movable in three dimensional directions. Further, the three-dimensional movement of the stage 11 may be driven by the drive section 3.

The light source 12 only needs to (i) be provided below the stage 11, (ii) illuminate the sample 23 from below, and (iii) have a light intensity enough for the analyzer 100 to carry out the analysis operation and for the image pickup section 7 to take an image. The light source 12 may be a conventional light source known to public, and its specific arrangement is not particularly limited. Examples of the light source 12 may encompass a halogen lamp, a xenon lamp, a tungsten lamp, and a light-emitting diode. Of these, the light-emitting diode is preferable because the light-emitting diode has a long light-emitting life.

Further, the slide glass 21 and the cover glass 22 may be the ones which are available in a conventional preparation known to public, and their specific arrangements are not particularly limited. For example, a slide for U-SCANNER (Registered Trademark) manufactured by TOYOBO Co., Ltd. may preferably be used.

Furthermore, the analyzer 100 may be provided with: a pouring section (pouring means) for taking the sample 23 and pouring, to the preparation 20, the sample 23 thus taken; a preparation supplying section (preparation supplying means) for supplying a preparation; and a conveying section (conveying means) for conveying the preparation 20 to the stage 11. (Each section (means) is not illustrated in the present embodiment.) More preferably, in addition to the sections (means), the analyzer 100 may be provided with: a rack supporting section (rack supporting means) for supporting a rack holding thereon a plurality of containers including a sample; and a rack conveying section (rack conveying means) for conveying the rack, inside the analyzer. With this arrangement, it is possible to carry out, in an automated manner, operation from a step for taking a sample to a step for displaying a result, merely by setting the sample. The above-mentioned member may be a member used in a conventional automatic analyzer known to public, and their specific arrangements are not particularly limited. For example, the analyzer may be provided with various members used in U-SCANNER (Registered Trademark) manufactured by TOYOBO Co., Ltd.

In a case where a tangible component in a urine sample is analyzed, the pouring section in the analyzer 100 is provided with the function for automatically focusing on a sample image of a tangible component. Further, in addition to means for taking the sample image, the pouring section may more preferably be provided with: means for stirring a urine liquid to be examined (i.e., a sample) in a sample container; means for taking and pouring the urine liquid to be examined which is stirred; means for adding a staining solution to be mixed with the urine liquid to be examined; means for pouring, to a space between a slide glass and a cover glass, a mixture solution obtained by the mixture of the urine liquid to be examined mixed and the staining solution; an image pickup stage for taking an image of the urine liquid to be examined which is placed on the slide glass; means for magnifying a sample image of a tangible component in the urine liquid to be examined; and means for identifying the component in the image by processing the image which is taken.

With this arrangement, after liquid to be examined (raw urine) is stirred by the stirring means, the liquid to be examined in a stirred state can be transferred to a process to be carried out by the pouring means. At this time, a centrifugation step is not necessary.

Further, the pouring section may be provided with means for storing a result obtained by processing the image which is taken and classifying the component in the image.

As the means for stirring urine liquid to be examined in a sample container, the following methods are assumed: a method using an additionally-prepared jig (e.g., a stirring stick) for stirring; a non-contact stirring method for stirring the urine liquid to be examined, by swinging the sample container or by using a microwave; or the like. Preferably, the means may be a method using a jig for sucking urine sample liquid to be examined. The jig for sucking urine sample liquid to be examined may be, for example, a probe. In this case, the probe itself may be provided with a stirring function. That is, the following methods are possible: a method for stirring urine sample liquid to be examined, by carrying out, at least once, a suction/discharge process for the urine sample liquid during a sucking process of the urine sample liquid; a method for carrying out the suction/discharge process while a position of the probe is changed; and a method for stirring urine sample liquid by moving the probe while the probe is used as a stirring stick. As such, providing the probe itself with the stirring function realizes a simpler analyzer arrangement. This attains reduction in space and cost.

The means for pouring urine liquid which has been stirred may use a probe or a tip. Moreover, using a disposable probe or tip further reduces a possibility of cross-contamination.

In the means for adding the staining solution to be mixed with urine liquid to be examined, a probe or a tip each of which is for taking and pouring a staining solution may be used. However, by sharing a probe between (i) the means for stirring the sample in the sample container and (ii) the means for adding the staining solution to be mixed with the urine liquid to be examined, it is possible to realize a simpler analyzer arrangement. This attains reduction in space and cost. Further, as well as in the method for stirring the sample in the sample container, it is preferable to mix the staining solution and the sample with each other in such a manner that (i) a predetermined amount of a sample (or a staining solution) is taken, (ii) the predetermined volume of the sample (or the staining solution) thus taken is caused to touch a probe sucking and holding a predetermined amount of a staining solution (or a sample), and (iii) a suction/discharge process is carried out so as to mix the sample and the staining solution with each other.

The means for pouring, to the space between the slide glass and the cover glass, the mixture solution obtained by the mixture of the liquid to be examined and the staining solution may be: a method in which a probe or a tip sucking and holding the mixture solution is put to the space so as to discharge the mixture solution thereinto; or a method in which the mixture solution is put onto an area allowing the mixture solution to come in contact with the space (i.e., a surface of the slide glass or the cover glass each of which constitutes the space) so that the mixture solution is flowed into the space due to capillary action.

In the analyzer of the present invention, the slide glass is used as the light-transmitting plate on which liquid to be examined (sample) is placed. However, the present invention is not limited to this, and the light-transmitting plate only needs to allow light to be transmitted therethrough and to be capable of holding thereon the liquid to be examined. Preferable examples of the light-transmitting plate may encompass a slide glass. Because the slide glass is used only once (i.e., disposable), there is no possibility of carry-over of a sample which has been previously examined or of contamination by a staining solution. This provides a highly-reliable measurement result. Material of the light-transmitting plate is not particularly limited, but only needs to have a light-transmitting property. Examples of the material may encompass plastic (synthetic resin) and glass. In a case where plastic is used as the material, the plastic may preferably be subjected to a physical and chemical process as needed so as to enhance its hydrophilic property.

As a method for enhancing the hydrophilic property, the following method is possible: a method for applying, in advance, a surfactant and/or the like onto a surface of the material which surface is to touch liquid to be examined. Further, the following method may preferably be adopted: a method for subjecting the material with a plasma discharge treatment or a corona discharge treatment.

Figure 6A:
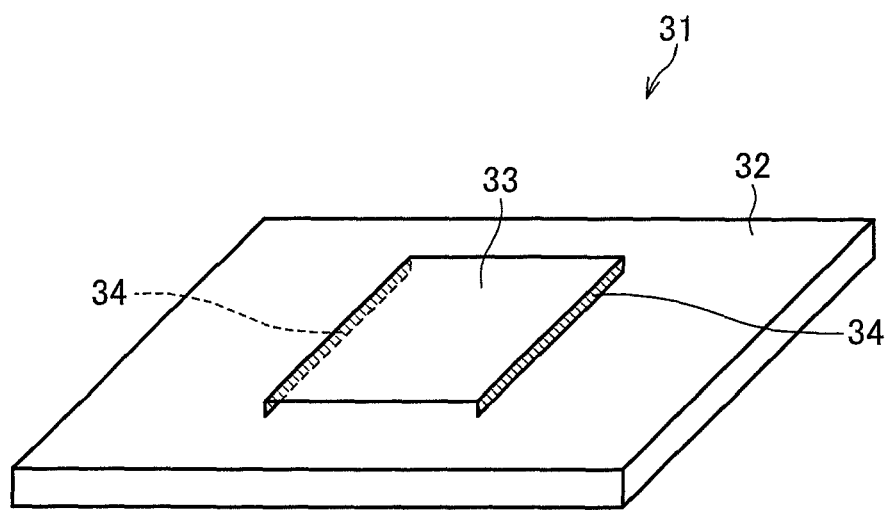
FIG. 6 (a) is a perspective view of a slide glass 31 integrating a cover glass.
Figure 6B:
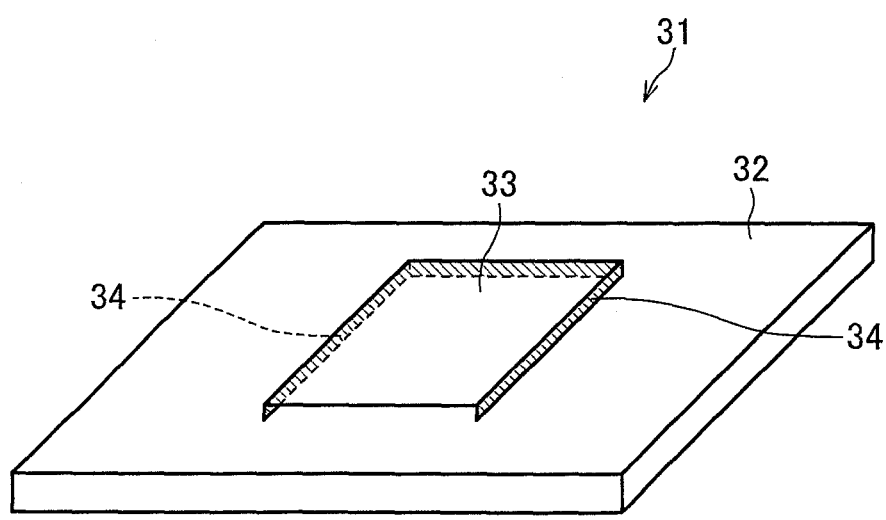

The liquid to be examined placed on the light-transmitting plate may be covered with the light-transmitting covering plate. The light-transmitting covering plate may be, for example, a cover glass. Material of the light-transmitting covering plate may be the same as that of the light-transmitting plate. However, the material of the light-transmitting covering plate is not particularly limited. FIG. 6 is a perspective view of a slide glass 31 integrating a cover glass, which is integrally made of a cover glass (i.e., a light-transmitting covering glass) and a slide glass (i.e., a light-transmitting plate). In FIG. 6 (a), two opposite sides of a cover glass 33 placed on a slide glass 32 are sealed with an adhesive 34 or the like, and another two opposite sides of the cover glass 33 are opened. In FIG. 6 (b), three sides of a cover glass 33 placed on a slide glass 32 are sealed with an adhesive 34 or the like, and one side of the cover glass 33 is opened, the one side being not any one of the three sides. When liquid to be examined is put to the one side which is opened, the liquid to be examined is flowed into a space between the slide glass 32 and the cover glass 33 due to the capillary action. That is, the liquid to be examined is put on the slide glass 32, which is the light-transmitting plate. As such, with the slide glass 31 integrating the cover glass, it is possible to easily and accurately pour a predetermined amount of liquid to be examined. This simplifies a troublesome sample preparing step for setting a cover glass at a slide glass, thereby saving labor in the step.

Further, the light-transmitting plate may be a multifunctional observation plate including a plate member provided with (i) an observation section on one side of the plate member and (ii) one or more recessed sections at a position on the one side, the position being not the position where the observation section is provided. The observation section includes the light-transmitting plate and the light-transmitting covering plate. The one or more recessed sections are provided at a position on the plate member, the position being not the position where the observation section is provided.

The recessed position may be: a reaction vessel in which liquid to be examined is mixed or reacted with a reagent (such as a staining solution) so as to obtain a liquid to be observed (sample); a heating vessel for heating liquid to be examined or liquid to be observed; a cleaning vessel for storing cleaning fluid for cleaning the probe or the tip which conveys, to the observation section, liquid to be observed; or a waste liquid vessel for storing fluid such as cleaning fluid which has been used for cleaning. Further, a vessel having a combination of the functions may also be possible. Furthermore, a necessary reagent (such as a staining solution) or cleaning fluid may be poured into the vessel, and the vessel may be sealed in advance with a film or the like, as needed.

Figure 12:
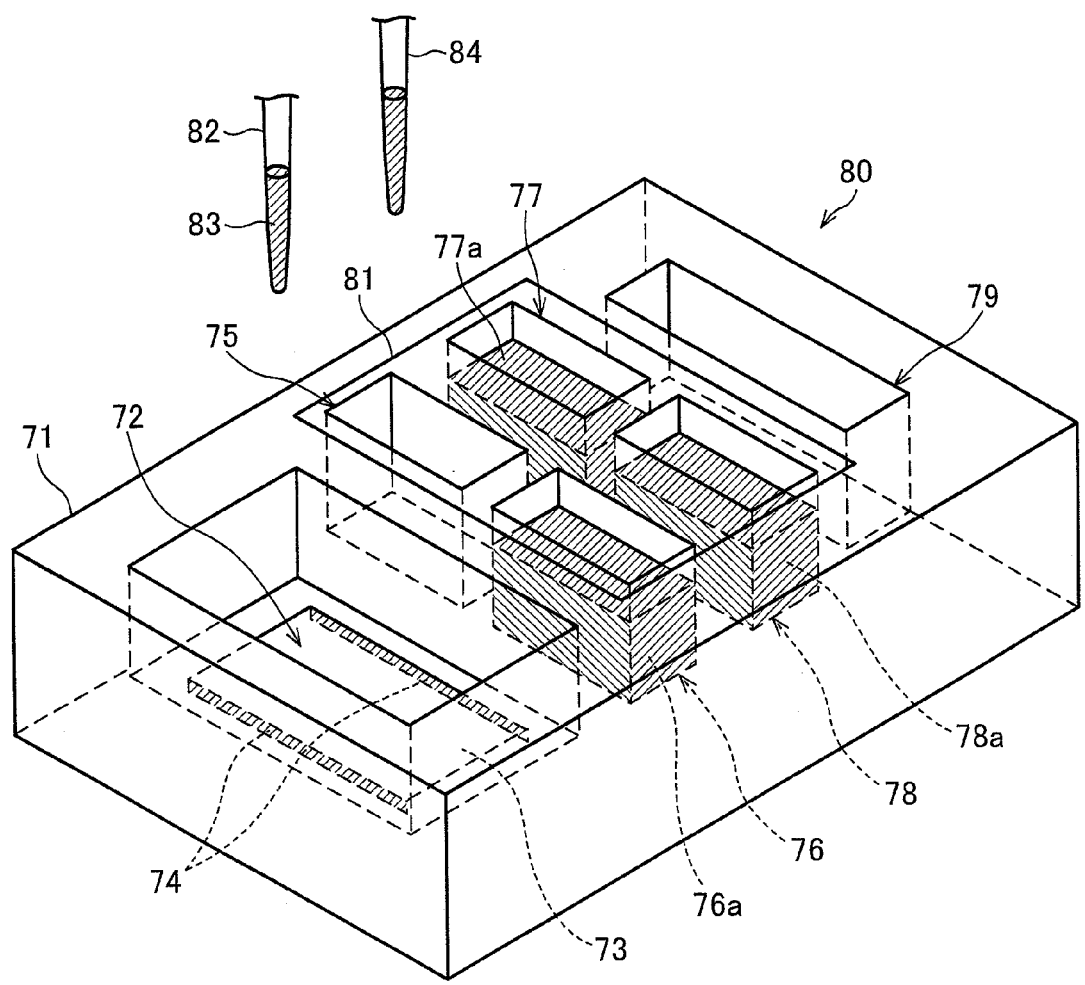
FIG. 12 is a perspective view illustrating one example of an arrangement of a multifunctional observation plate, which is a "light-transmitting plate" and used for an analysis of a tangible component in the present invention.

One example of the multifunctional observation plate used in an analysis of a tangible component is illustrated in FIG. 12 (a perspective view). A multifunctional observation plate 80 according to the present invention includes a plate member 71. The plate member 71 is provided with (i) an observation section 72 on one side of the plate member 71 and (ii) one or more recessed sections (75 to 79) at a position on the one side, the position being not the position where the observation section 72 is provided. The observation section 72 is formed by placing, on the plate member 71, a sheet member 73 having a light-transmitting property. The observation section 72 is for observing liquid to be observed which is placed between the plate member 71 and the sheet member 73.

In the plate member 71, at least an area on which the sheet member 73 can be placed (i.e., an area which can be the observation section 72) is made of light-transmitting material. This allows light to be transmitted from one side of the area to another side. A part (two opposite sides in FIG. 12) of a periphery of the sheet member 73 is bonded to the plate member 71 by an adhesive 74. The recessed section 75 is a reaction vessel in which liquid to be examined is reacted with a reagent so as to obtain a reaction solution. The recessed section 76 is a reagent vessel for storing the reagent. In the recessed section 76, a reagent 76a is stored. The recessed sections 77 and 78 (cleaning fluid vessels) store cleaning fluid (77a and 78a) for cleaning probes (82 and 84), respectively. The recessed section 79 is a waste liquid vessel for storing cleaning fluid which has been used for cleaning the probes 82 and 84. The reaction vessel (i.e., the recessed section 75), the reagent vessel (i.e., the recessed section 76), and the cleaning fluid vessels (i.e., the recessed sections 77 and 78) are sealed with a sealing member 81 of a film-shape. Further, another recessed section may be additionally provided so as to store liquid to be examined which is not reacted with the reagent yet.

In FIG. 12, the following procedures are carried out so that (i) liquid to be examined is reacted with a reagent for the purpose of obtaining liquid to be observed and (ii) the liquid to be observed thus obtained is observed at the observation section 72:

(1) The probe 82 sucking and holding liquid 83 to be examined breaks through the sealing member 81 and is inserted into the reaction vessel (i.e., the recessed section 75) so as to pour thereinto the liquid 83 to be examined;

(2) The probe 84 breaks through the sealing member 81 and is inserted into the reagent vessel (i.e., the recessed section 76) so as to suck and take a predetermined amount of a reagent;

(3) The probe 84 is inserted into the reaction vessel (i.e., the recessed section 75) so as to pour thereinto the reagent thus taken;

(4) The liquid to be examined and the reagent are reacted with each other in the reaction vessel (i.e., the recessed section 75) for a predetermined period of time so as to so that liquid to be observed (reaction solution) is obtained, and then the probe 82 or the probe 84 sucks and takes a predetermined amount of the liquid to be observed;

(5) The liquid to be observed thus taken is dripped onto one side of the observation section 72 which one side is not bonded by the adhesive 74, and then the liquid to be observed is flowed into a space between the sheet member 73 and the plate member 71 due to the capillary action;

(6) After the liquid to be observed thus flowed spreads over the whole surface of the observation section 72, the liquid to be observed is observed by a medical technologist or a tangible component analyzer so that an analysis of a tangible component is carried out;

(7) Then, the probe 82 and the probe 84 break through the sealing member 81 and are inserted into the cleaning fluid vessel (i.e., the recessed section 77) storing the cleaning fluid 77a so as to suck and take the cleaning fluid 77a;

(8) The cleaning fluid 77a thus taken by the probe 82 and the probe 84 is poured into the waste liquid vessel (i.e., the recessed section 79) as waste liquid;

(9) Further, the probe 82 and the probe 84 break through the sealing member 81 and are inserted into the cleaning fluid vessel (i.e., the recessed section 78) so as to suck and take the cleaning fluid 78a, and the cleaning fluid 78a thus taken is also poured into the waste liquid vessel (i.e., the recessed section 79) as waste liquid; and

(10) After all the steps are completed, the multifunctional plate 80 is disposed of.

As described above, with the multifunctional observation plate 80 illustrated in FIG. 12, it is possible to carry out, by using a single plate, a process from (i) reaction between liquid to be examined and a reagent to (ii) cleaning of a probe.

Figure 13:
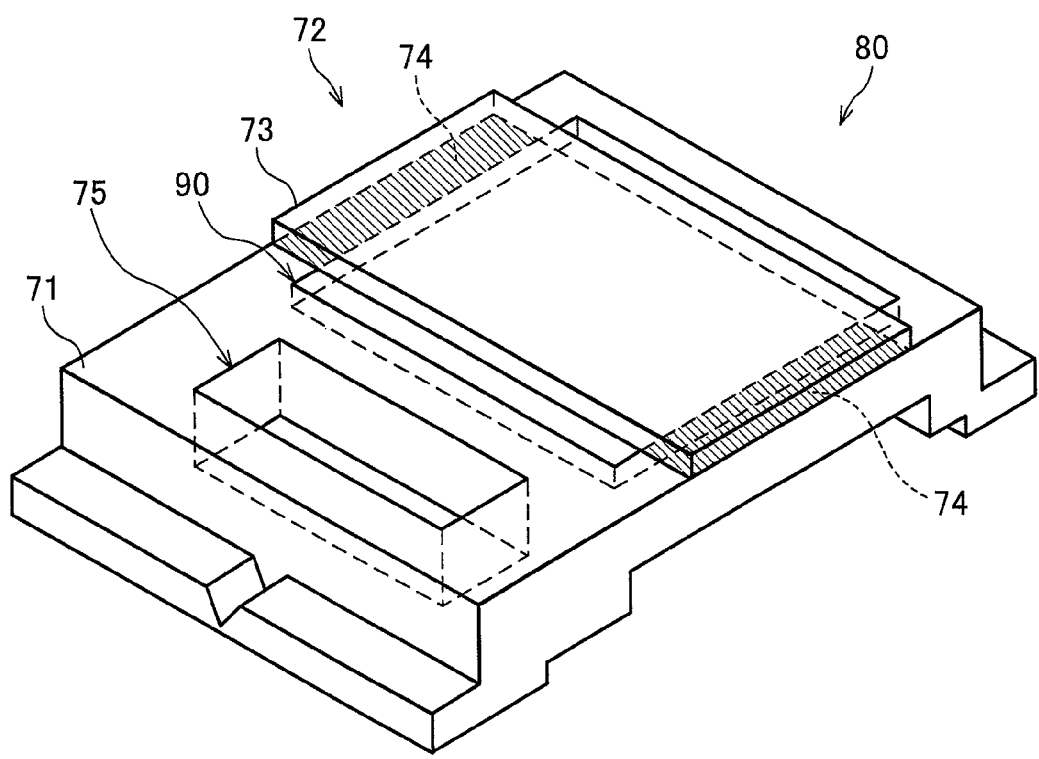
FIG. 13 is a perspective view illustrating another example of the arrangement of the multifunctional observation plate, which is the "light-transmitting plate" and used for the analysis of the tangible component in the present invention.

FIG. 13 is a perspective view illustrating another example of the multifunctional observation plate for an analysis of a tangible component in the present invention. In the example illustrated in FIG. 13, a multifunctional observation plate 80 is realized by a plate member 71 provided with one observation section 72 and one recessed section 75. The plate member 71 is made of light-transmitting material only. In a case where liquid to be examined is used as liquid to be observed as it is, the recessed section 75 serves as the heating vessel for heating the liquid to be examined. In a case where liquid to be observed is a reaction solution obtained by reaction between liquid to be examined and a reagent, the recessed section 75 serves as (i) the reaction vessel in which the liquid to be examined is reacted with the reagent or (ii) a reaction vessel and heating vessel. The observation section 72 is realized by the plate member 71 provided with a sheet member 73 having a light-transmitting property.

In the example illustrated in FIG. 13, a recessed section 90 is provided at a part of the plate member 71 which part is to serve as the observation section 72. Two opposite sides of the sheet member 73 having the light-transmitting property are bonded to a top surface of the plate member 71 so that the sheet member 73 covers an opening of the recessed section 90 except for a part of the opening. The shaded areas in FIG. 13 indicate areas in which the sheet member 73 is bonded to the top surface of the plate member 71 by means of an adhesive 74. Liquid to be examined or a reaction solution is poured into the recessed section 90 through a space between the plate member 71 and the sheet member 73 having the light-transmitting property, and then the liquid to be examined or the reaction solution thus poured is observed.

The image pickup stage for taking the image of the liquid to be examined which is placed on the slide glass is not particularly limited, but only needs to be capable of holding the light-transmitting plate thereon. However, the image pickup stage may preferably be the one which is movable so as to shift the image pickup position one from another. The movement may be carried out manually. However, it is preferable that the movement is mechanically carried out by means of, for example, a servo motor, a stepping motor, or a linear motor.

The image pickup means may be a digital camera, a CCD color video camera, or the like. Further, it is preferable that the image pickup means is provided with a function (i.e., the automatic focusing function) for automatically focusing on a sample image of a tangible component. The magnifying means may be (i) the one for optically magnifying a sample image which is not taken yet or (ii) the one for subjecting, to digital processing or the like, a sample image which has been taken so as to magnify the sample image. Specifically, the magnifying means may be: a zoom lens attached to the camera; an objective lens; or the like.

A size of a tangible component in liquid to be examined ranges from some μm (e.g., blood cells and a fungus) to some hundreds μm (e.g., a cast). In view of this, it is preferable that the magnifying means (objective lens) for magnifying a sample image of a tangible component in urine liquid to be examined has two or more magnification scales, rather than having only one magnification scale. The magnifying means having two or more magnification scales is capable of carrying out a more accurate analysis of a tangible component, from small one to large one. Further, the magnification scale of the magnifying means may be varied in a continuous manner. The magnification scale may be determined depending on a tangible component as needed.

The identifying means for identifying a component in the image by processing an image which is taken carries out a classification and an identification of a tangible component in an image which is taken, in accordance with a shape and/or the like of the tangible component. The identifying means may preferably be provided with (i) a function for working out an analysis result from all identification results obtained in a preset number of visual fields and (ii) a function for outputting the analysis result via an output device. The "preset number of visual fields" herein means the number of visual fields (images) whose images are to be taken. Further, the identifying means may preferably be provided with a memory or the like for temporarily storing an image which is taken.

Examples of the identifying means may encompass: a computer including a program for causing the computer to carry out the identifying process; and an identifying device including a logical circuit. Of these, it is preferable to use the computer as the identifying means, because this makes it possible to carry out the whole control by means of software, the whole control including: operation of each step; image processing; memory; calculation; output; and the like.

The identifying means may preferably include a learning function. The identifying means including the learning function can provide a highly accurate and detailed measurement result. It is possible for the identifying means to learn (1) a range setting of color extraction in which colors are separated according to brightness and chromaticity based on red, green, and blue, (2) a range setting of image binarization processing including spot removal, line segment writing, and image separation, and (3) a range setting of a characteristic amount (such as an area, circularity, a circle-equivalent diameter, a perimeter, an absolute maximum length, an X/Y ratio in a Feret's diameter, an X/Y ratio in a maximum chord length, and a ratio between a short axis length and a long axis length) of an image, for the purpose of carrying out an identification.

In the image processing carried out by the identifying means, a tangible component is classified and identified by means of the software, in accordance with a shape of the tangible component. Therefore, it is possible for the identifying means to carry out a highly-accurate classification of components having apparently different shapes (e.g., a cast and a flat epithelium). On the other hand, it is inevitable that accuracy in an analysis of components having a similar shape (e.g., a small renal epithelial cell, a red blood cell, a white blood cell, and a fungus) is decreased.

In view of this, the analyzer according to the present invention is additionally provided with means for adding a reagent (such as a staining solution) to liquid to be examined, for the purpose of facilitating an identification of a component. Further, a method according to the present invention is provided with a step for adding a reagent (such as a staining solution) to liquid to be examined, for the purpose of facilitating an identification of a component. These arrangements helps with a classification of components having a similar shape, thereby improving the accuracy in an analysis.

The reagent is not particularly limited. The reagent may be the one including at least one component used in any one of the following commonly known methods: a Sternheimer-Malbin staining method (an SM staining method); a Sternheimer staining method (an S staining method, an NS staining method, or a variation of the Sternheimer staining method); a Prescott-Brodie staining method; a Behre-Muhlberg staining method (a BM staining method); a Sudan III staining method; a Lugol staining method; a hemosiderin staining method; a Papanicolaou staining method; a 4-chloro-1-naphthol method; a Field staining method; a Quaglino-Flemans method; a Kaplow method; a Sato-Sekiya method; a Berlin blue method; a Giemsa staining method; a Wright staining method; a Pappenheim staining method; a Congo red staining method; a methylgreen-pyronin staining method; an alcian blue staining method; a Shorr staining method; a Feulgen staining method; an oil red O staining method; a Brecker method; a Heinz body staining method; a neutral red-Janus green supervital staining method; a brilliant cresyl blue staining method; and the like (*Rinsho-Kensa Atorasu* 1, *Nyo-Chinsa* (2nd edition) [Atlas of Clinical Laboratory Examination 1, Urinary Sediment (2nd edition)], published by Ishiyaku Publishers, Inc.; *Rinsho-Kensa Gijutsu Zensho* 3, *Ketsueki-Kensa* [Complete Book of Techniques of Clinical Laboratory Examination 3, Blood Test], published by Igaku-Shoin Ltd.; *Rinsho-Kensa-Ho Teiyou* [Outline of Clinical Laboratory Examination Methods], published by Kanehara & Co., Ltd.; *Senshoku-Ho no Subete, MEDICAL TECHNOLOGY Bessatsu* [All About Staining Methods, Additional Volume of MEDICAL TECHNOLOGY], published by Ishiyaku Publishers, Inc.). For example, the followings are possible: (i) a reagent obtained by a combination of some kinds of staining solutions and additives selected out of a plurality of kinds of staining solutions and additives used in a certain staining method; and (ii) a reagent obtained by a combination of a plurality of kinds of staining solutions used in different staining methods.

Further, in order to improve preservation stability and antiseptic performance of the staining solution, the staining solution may include a commonly known antiseptic (antibacterial) agent such as: various kinds of antibiotics; EDTA salts; a boric acid; a citric acid; $NaN_3$; proclin; benzisothiazolone; pyrithione; and N-methylisothiazolone. Furthermore, in order to maintain the staining solution at an optimum pH, the staining solution may include various kinds of buffer solutions. Moreover, in order to maintain a shape of a tangible component, the staining solution may include various kinds of salts (e.g., the EDTA salts, a carbolic acid salt, an oxalate, a citrate, NaCl, KCl, $CaCl_2$, and $AlCl_3$), various kinds of sugars (e.g., glucose, fructose, galactose, maltose, xylitol, and sorbitol), cyclodextrin, or glutaraldehyde. Further, in order to remove an insoluble substance which interferes with a measurement, the staining solution may include various kinds of surfactants or enzymes.

Further, in a case where it seems to be difficult to obtain a sufficient result by means of a classification according a shape of a component, it is preferable that: (i) in the analyzer according to the present invention, the identifying means is provided with a function for working out the amount of a tangible component based on an optical characteristic amount derived from the tangible component; and (ii) in the method according to the present invention, the amount of a tangible component is worked out based on an optical characteristic amount derived from the tangible component.

For example, in a case where the amount of a microbe such as a bacterium in liquid to be examined is measured, a luminous reagent may be added to the liquid to be examined for the purpose of further improving accuracy in an analysis. However, a degree of staining varies by a state (e.g., killed or viable) of a bacterium. This reduces accuracy in an analysis. In view of this, in order to further improve the accuracy in the analysis, the following step may be provided: a step for measuring the amount of ATP (adenosine triphosphate) in liquid to be examined. This step utilizes the fact that a microbe generates ATP. With this, it is possible to accurately measure the amount of bacteria in liquid to be examined. The measurement of the amount of ATP may be carried out by detecting, with use of an ATP reagent including a luciferase and a luciferin, the amount of emitted light (optical characteristic amount), which has relevance to the amount of ATP (refer to the following chemical formula).

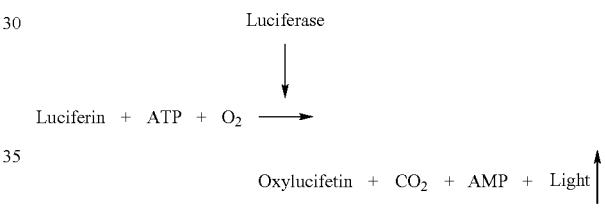

Further, it is preferable for the analyzer of the present invention to include means (image storing device) for storing a result obtained by processing an image which is taken and identifying the component in the image. Examples of the means may encompass an auxiliary storage device having a large capacity, such as a magneto-optical disk, a fixed disk, a digital video disk, and a CD-R. Examples of the output device used in the analyzer of the present invention may encompass: an output device such as a CRT display, a liquid-crystal display, and a printer; and the auxiliary storage device.

In a case where the display is used as the output device, the output device may be provided with the following functions: a function for displaying, in addition to a measurement result and image data, items such as time and a current state of the analyzer (e.g., a measurement state with respect to a sample, assumed measurement end time or remaining time required for a measurement each of which time is for samples or a selected sample, the amount of waste liquid in a waste liquid tank, a remaining amount of a purified water in a purified water vessel, a remaining amount of a reagent, a remaining amount of a cleaning agent, and the number of remaining slide glasses), in accordance with a selected menu; and a function for magnifying and displaying information which is selected so that the information can be read from a distance.

In the analyzer of the present invention, the identifying means may be provided with: a function for classifying, into an item entitled "other components", a tangible component which cannot be classified; and/or a function in which (i) an image including a tangible component which has been classified into the item entitled "other components" is displayed later, (ii) the tangible component is judged by a medical technologist directly with his/her eyes, and (iii) a judgment result made by the medical technologist is added to data or the data is modified in accordance with the judgment result.

The analyzer of the present invention may be provided with a function for remotely selecting an indication menu of the display and remotely operating the analyzer with use of a remote controlling device. Further, the analyzer of the present invention may be provided with a function for giving a warning by means of display indication, sound, or a signal in a case where: an accident occurs; the waste liquid tank is filled up; a remaining amount/number of purified water, a reagent, a cleaning agent, a slide glass, or the like is small; or the like.

In order to deal with an urgent analysis, the analyzer of the present invention may be provided with a function for placing priority on an urgent sample (i.e., a sample required to be analyzed urgently) and carrying out an analysis of the urgent sample following a sample currently analyzed; or a function for temporarily stopping an analysis which is currently under operation so as to analyze an urgent sample immediately. In this case, because the urgent analysis needs to be carried out immediately, it is preferable that the analyzer is provided with, for example, an urgent analysis button. It is possible to cause the analyzer to start an urgent analysis merely by operating the urgent analysis button.

It is possible to easily carry out the method according to the present invention by using the above-mentioned analyzer of the present invention. That is, in the method, the following steps are carried out: a step for automatically placing, on a light-transmitting plate, liquid to be examined; a step for magnifying, by means of the magnifying means, a sample image of a tangible component in the liquid to be examined; a step for automatically focusing on the sample image of the tangible component and taking the sample image of the tangible component by means of the image pickup means; and a step for identifying, by means of the identifying means, the component in the image thus taken, by processing the image. As such, with use of the analyzer of the present invention, it is possible to carry out the method according to the present invention in a totally-automated manner.

Next, the following describes specific analysis operation carried out by the analyzer 100. In the present embodiment, for convenience of description, an analysis of a tangible component in urine is described as an example. Of course, the present invention is not limited to this.

Firstly, a step for preparing a preparation 20 of a sample 23 is described. A necessary amount of urine is taken from a rack holding a plurality of containers (not illustrated) such as a test tube, and the urine thus taken is poured to a predetermined reaction vessel (not illustrated). At this time, for the purpose of pouring a uniform sample, the urine may be taken after being stirred. Further, in a case of using a container to which individual recognition means (such as a bar code) is attached in advance, the individual recognition information may be read by a bar-code reading device during the poring process.

Next, a staining solution (e.g., a staining solution for U-SCANNER (Registered Trademark) manufactured by TOYOBO Co., Ltd.) for staining a tangible component in urine is poured to the reaction vessel so that a tangible component in the urine is stained. The urine and the staining solution are mixed well in the reaction vessel, and then a predetermined amount of the urine thus stained is taken and poured to a slide glass 21. Then, a cover glass 22 is placed on the slide glass 21. The cover glass 22 and the slide glass 21 are left at rest for a few minutes so that the urine thus poured spreads over uniformly. Thus, a preparation 20 holding the sample 23 is prepared.

The preparation 20 thus prepared in the above-mentioned step is placed on the stage 11. As described above, the stage 11 is arranged so as to be capable of freely (i) moving the preparation 20 in the x-axis, y-axis, and z-axis directions, that is, in three dimensional directions and (ii) stopping moving the preparation 20. After the preparation 20 is placed on the stage 11, light emitted from the light source 12 is collected to the preparation 20. Steps following this process are unique control operation of the analyzer according to the present invention, and are described in detail in accordance with a process flow illustrated in FIG. 4 and FIG. 5.

Firstly, in step 1 (hereinafter, "step" is simply referred to as "S") of FIG. 4, the control section 5 controls the automatic focusing section 4 so that the objective lens 1 focuses on the preparation 20. In the focusing operation, a subject to be focused may be either of the slide glass 21 or the cover glass 22. A method of the focusing operation may be any one of the foregoing automatic focusing methods. Further, for example, as described in Patent Document 2, a focus mark may be provided. The focus mark is used as a reference position in focusing to one surface of either of the slide glass 21 or the cover glass 22. Carrying out the focusing operation by focusing on the focus mark makes it possible to easily focus on the slide glass 21 or the cover glass 22.

It is preferable that the step for the focusing operation with respect to the preparation 20 is carried out in a few minutes in which the preparation 20 is left at rest so that the sample 23 spreads over uniformly after the predetermined amount of the sample 23 is taken from the reaction vessel and poured to the slide glass 21. This makes it possible to carry out the focusing operation step without extending processing time of the analyzer 100. With the process in S1, it is possible to carry out the focusing operation for each preparation 20. This solves a problem caused by the manufacturing allowance of the preparation 20. The problem is caused as follows: (i) a difference in thickness between preparations 20 slightly varies a depth of a focus point of preparations 20, and (ii) this causes a difference in focus point between the preparations 20, thereby preventing accurate automatic focusing operation for the preparations.

Next, in S2, the control section 5 controls the driving section 3 so as to vary a relative distance between the objective lens 1 and the preparation 20, and thereby to move the objective lens 1 a predetermined distance from a focus position obtained in S1 in the vertical direction (i.e., the z-axis direction). In the present embodiment, the stage 11 is driven in the z-axis direction so as to vary that the distance between the preparation 20 and the objective lens 1. However, the present invention is not limited to this. Instead of the stage 11, the objective lens 1 may be moved.

This process is for making offset movement so as to move the objective lens 1 a predetermined distance for the purpose of setting an analysis start position at which an observation of a tangible component is started. That is, the control section 5 sets, as the predetermined analysis start position, a position to which the objective lens 1 is moved by means of the offset movement of the predetermined distance from the position where the objective lens 1 is focused on the slide glass 21 or the cover glass 22.

The "predetermined distance" is not particularly limited, but may be set as needed depending on a type of a preparation or a sample, a tangible component to be analyzed, an analysis condition, or the like. That is, the process carried out in S2 is for making the offset movement of the objective lens 1 which has been focused on the preparation 20 in S1 and thereby moving an observation position of the objective lens 1 from the focus position to a "position at which an analysis is desired to be started", which is in a space between the slide glass 21 and the cover glass 22.

Specifically, for example, in a case where a tangible component having a low specific gravity is to be analyzed, the analysis start position may be shifted to the vicinity of a position right below the cover glass 22. On the other hand, in a case where a tangible component having a high specific gravity is to be observed, the analysis start position may be shifted to a position in the vicinity of the slide glass 21. Further, in a case where a tangible component having an intermediate specific gravity is to be analyzed, the analysis start position may be shifted to a position just midway between the slide glass 21 and the cover glass 22.

The processes carried out in S1 and S2 are for avoiding the effect caused by the difference in the focus point due to the manufacturing allowance of the preparation. Therefore, for example, if quality of a preparation is so high that the effect caused by the manufacturing allowance hardly needs to be considered, the processes in S1 and S2 may be omitted. In a case where the manufacturing allowance of the preparation does not need to be considered, it is possible to omit the processes in S1 and S2, for example, by setting the analysis start position as an initial value in advance. Omitting the processes in S1 and S2 increases a processing speed of an analysis, thereby improving efficiency.

Next, in S3, the control section 5 controls the automatic focusing section 4 and/or the drive section 3 so that automatic focusing operation is carried out in a range from the analysis start position, which is set in S2, to a preset analysis end position. That is, after the control section 5 changes the observation position of the objective lens 1 by means of the offset movement in S2, the control section 5 controls so as to carry out the automatic focusing operation. Specifically, the automatic focusing operation is carried out such that the control section 5 causes the objective lens 1 to move from (i) the observation position to which the objective lens 1 has been moved to (ii) a preset observation position (i.e., the control section 5 causes the objective lens 1 to move a predetermined distance in the z-axis direction). The automatic focusing operation in S3 may preferably be carried out by means of the foregoing methods.

The process in S3 is for carrying out the automatic focusing operation, from the analysis start position (which is set in S2), within a range in which an analysis is desired to be carried out. The "preset analysis end position" in S3 is not particularly limited, but may be set as needed depending on a type of a sample, a tangible component to be analyzed, an analysis condition, or the like. Specifically, for example, the preset analysis end position may be the one allowing the automatic focusing operation to be carried out in such a manner that the objective lens 1 is caused to move, from the analysis start position, a distance (approximately some tens µm through some hundreds µm) in which a tangible component in an object to be analyzed is assumed to be present. That is, in S3, the automatic focusing operation is carried out in the range from the analysis start position to the analysis end position, for the purpose of carrying out an analysis of the tangible component. The "analysis start position" and the "analysis end position" are not particularly limited, but may be set arbitrarily. However, a distance (in the z-axis direction) between the "analysis start position" and the "analysis end position" may preferably be, for example, in a range from 30 µm to 1000 µm, more preferably be in a range from 50 µm to 800 µm, and further more preferably be in a range from 80 µm to 500 µm. These ranges are based on a specification of a generally-used preparation. According to one example of the specification of the generally-used preparation, a distance (i.e., substantially an area in which a substance to be measured is included) between a top surface of a slide glass and a bottom surface of a cover glass in the z-axis direction is 80 µm, and a distance (i.e., a distance between the top surface of the slide glass and an outer surface of the cover glass, the distance including a thickness of the cover glass) between the top surface of the slide glass and a top surface of the cover glass is 470 µm. Therefore, carrying out an analysis in the foregoing ranges makes it possible to surely carry out an analysis of a tangible component existing in a preparation.

Subsequently, in S4, the focus state detecting section 2 detects whether or not the focus state is obtained as a result of the automatic focusing operation carried out in S3. For example, in a case where the method for causing the stage 11 to move a very short distance in the z-axis direction at every predetermined cycle is adopted as the automatic focusing operation, the focus state detecting section 2 may be arranged so as to (i) set, as an evaluation value, variance of a luminance level obtained at every cycle, (ii) detect a timing at which the evaluation value obtains a minimum value, and (iii) determine that a position of the stage 11 at the timing is a position in a focus state.

Next, if it is judged that the focus state detecting section 2 detects the focus state in S5, the judgment section 6 judges, in S6, that a tangible component is present in a focus position at which the focus state is obtained. Subsequently, in S7, the image pickup section 7 obtains an image of the tangible component in the focus position. Then, the procedure proceeds to S8.

Figure 3:
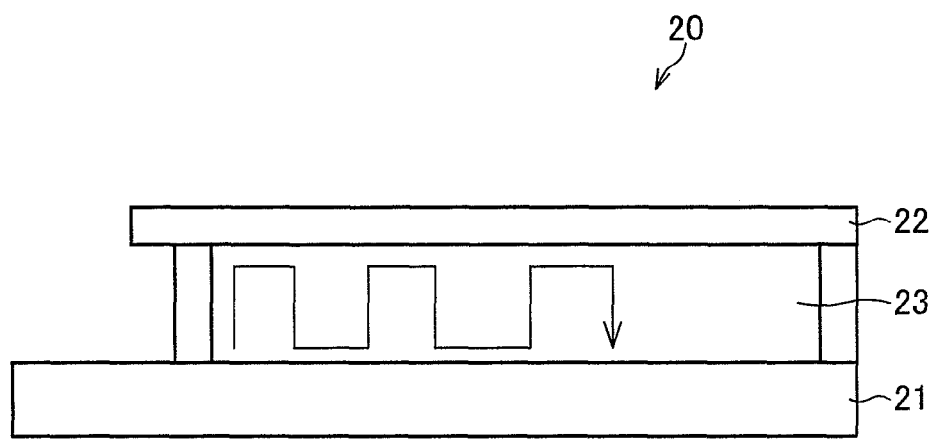
FIG. 3 is a schematic view of one example of a method for shifting a visual field one from another in the analyzer according to one embodiment of the present invention.

After the image is obtained in S7, the analysis operation in a visual field under operation is stopped in S8. Subsequently, in S9, the control section 5 controls the drive section 3 so as to shift the visual field to another visual field and carry out an analysis therein. That is, when the judgment section 6 judges, in S6, that the tangible component is present, the control section 5 controls the automatic focusing section 4 and/or the drive section 3 so as to stop the automatic focusing operation at the focus position which has been judged to have the tangible component. Then, the control section 5 changes, in the horizontal direction (in the x-axis and y-axis directions), the relative position between the objective lens 1 and the sample 23, for the purpose of carrying out another analysis of a tangible component in another visual field. As described later, it is preferable that the shifting of the visual field is repeatedly carried out a predetermined number of times. However, it is particularly preferable that the shifting of the visual field is carried out in a manner as illustrated in FIG. 3. According to the manner, the amount of movement of the stage 11 is reduced as much as possible, thereby reducing time taken for the shifting as much as possible.

A method for shifting of a visual field to "another visual field" is not particularly limited, but may be carried out in various kinds of ways. However, "avoiding shifting to a position adjacent to a position in which an analysis has been carried out" is preferable for the purpose of preventing overlap between visual fields. The "another visual field" may be arbitrarily and freely set by a user. In this case, for example, the "another visual field" may be set such that an analysis is carried out in some visual fields in a certain direction (in the x-axis and y-axis directions) and then an analysis is carried out in some visual fields in another direction. Instead, the "another visual field" may be randomly set by using a random number table or the like.

Next, in S10, in a case where another analysis of a tangible component is carried out in "another visual field" which is obtained in S9, the control section 5 controls so as to carry out automatic focusing operation only in a predetermined distance (area) in the vertical direction (in the z-axis direction), the predetermined distance (area) being in the vicinity of the focus position which has been judged, in S6, to have the tangible component. That is, in a case where an analysis is carried out in a plurality of visual fields, in this process, an analysis in a subsequent visual field(s) following a preceding visual field is/are carried out only in the vicinity of a position which has been judged to have a tangible component in an analysis carried out in the preceding visual field. This is based on knowledge originally found by the inventors. The knowledge is as follows: "If a tangible component is judged to be present in a certain visual field, there is a high possibility that a tangible component is also present at the same position (the same position on the z-axis) in other visual fields". This process eliminates need for carrying out the analysis operation with the initial setting every time a visual field is shifted one from another, thereby allowing an effective analysis.

Specifically, in this process, for example, the automatic focusing operation may be carried out in a predetermined distance ahead and behind (along the z-axis direction) the focus position which has been judged, in S6, to have the tangible component. The "predetermined distance" in this step may be arbitrarily set, and is not particularly limited. However, it is preferable that the "predetermined distance" is in a range from 5 μm to 100 μm, more preferably in a range from 10 μm to 80 μm, and further more preferably in a range from 30 μm to 60 μm. These ranges are preferable because of the following reason: It is known that, in a case where a urine sample is analyzed by using the preparation of the foregoing specification, distribution of tangible components in the z-axis direction varies between persons, since urine samples of the different persons have different specific gravity, different amounts of a tangible component which is contained, different viscosity, and/or the like, respectively. It has been confirmed through an experiment that tangible components are distributed in a range from approximately 30 μm to approximately 60 μm. Therefore, carrying out an analysis in these ranges makes it possible to surely carry out an analysis of a tangible component, without being affected by such a difference between persons.

If a focus state is detected in S11, the judgment section 6 judges, as well as in S6, that a tangible component is present (S12). Then, in S13, the image pickup section 7 obtains, as well as in S7, an image of the tangible component. After that, the procedure proceeds to S16.

On the other hand, when no focus state is detected in S11 and the automatic focusing operation is ended, the judgment section 6 judges that no tangible component is present in the visual field under operation (S14). Then, the image pickup section 7 obtains an image of the sample 23 at a position (analysis end position) where the automatic focusing operation is ended (S15). After that, the procedure proceeds to S16.

After the image is obtained in S13 or S15, the analysis operation in the visual field under operation is stopped in S16. After that, in S17, the control section 5 judges whether or not an analysis has been completed in a predetermined number of visual fields (e.g., a few tens of visual fields, and more preferably 50 to 100 visual fields). If the analysis has been completed in the predetermined number of visual fields, the process is ended. On the other hand, if the analysis has not been completed in the predetermined number of visual fields, the procedure returns to S9. Then, the processes (S10 to S17) for carrying out automatic focusing operation in another visual field are carried out again.

Subsequently, the following describes a process to be carried out in a case where the focus state detecting section 2 does not detect the focus state in S5 and the automatic focusing operation is ended.

Figure 4:
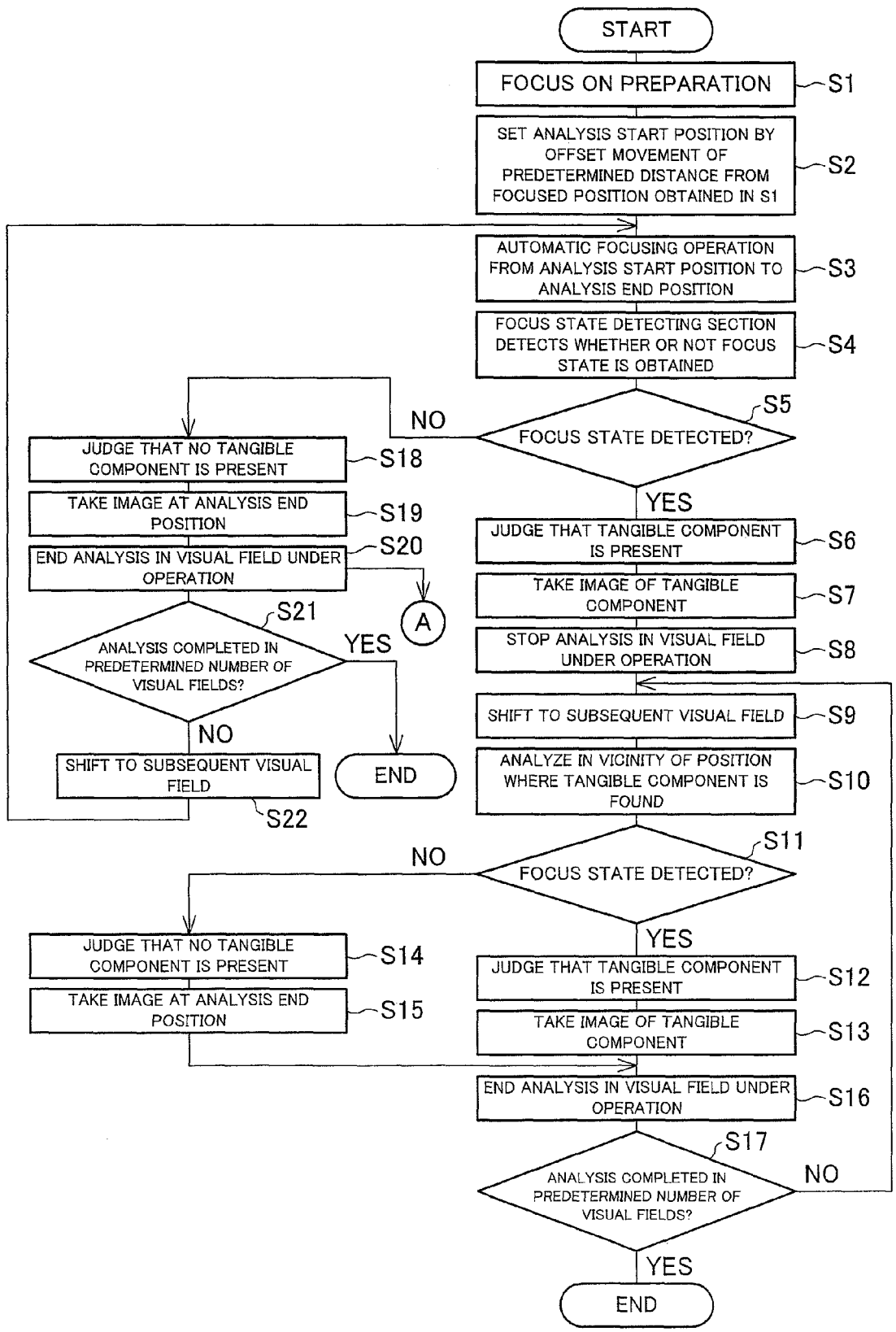
FIG. 4 is a view illustrating one example of a process flow of the analyzer according to one embodiment of the present invention.

As indicated in S18 in FIG. 4, in a case where the focus state detecting section 2 does not detect the focus state in S5 and the automatic focusing operation is ended, the judgment section 6 judges that no tangible component is present in the visual field under operation.

Subsequently, in S19, the image pickup section 7 obtains an image of the sample 23 at a position (analysis end position) where the automatic focusing operation is ended. Then, after the image is obtained in S19, the analysis operation is stopped in the visual field under operation in S20.

After that, in S21, the control section 5 judges whether or not an analysis has been completed in a predetermined number of visual fields (e.g., a few tens of visual fields, and more preferably 50 to 100 visual fields). If the analysis has been completed in the predetermined number of visual fields, the process is ended. On the other hand, if the analysis has not been completed in the predetermined number of visual fields, the procedure returns to S22. Then, the control section 5 controls so as to shift the visual field to another visual field.

In S22, the control section 5 controls the drive section 3 so as to shift the visual field to another visual field and to carry out an analysis therein. That is, if the judgment section 6 judges, in S18, that no tangible component is present in the visual field under operation, the control section 5 controls the automatic focusing section 4 and/or the drive section 3 so as to change the relative position between the objective lens 1 and the sample 23 in the horizontal direction (in the x-axis and y-axis directions), for the purpose of carrying out another analysis of a tangible component in another visual field.

Subsequently, in a case where said another analysis of the tangible component is carried out in said "another visual field" obtained in S22, the control section 5 controls the automatic focusing section 4 and/or the drive section 3 again so as to carry out automatic focusing operation in the range from the analysis start position (which is set in S2) to the analysis end position (which is set in advance). That is, in this case, after the process in S22 is carried out, the procedure returns to S3. This means that the automatic focusing operation is carried out again so as to carry out an analysis of a tangible component. The description of subsequent steps to be carried out in said "another visual field" is omitted here because the steps are similar to those in the description above (S3 to S21).

As described above, with the analyzer 100, it is possible to judge whether or not a tangible component is present in a sample 23 held in a preparation 20. Further, if a tangible component is present, it is possible to analyze the tangible component with efficiency and high accuracy.

Furthermore, if it is determined that no tangible component is present in a certain visual field, the analysis operation with the initial setting (i.e., the operation for extensively observing an area where a tangible component is assumed to be present) is carried out again, for the purpose of checking whether or not a tangible component is present in another visual field. This increases a possibility of finding a tangible component, thereby improving detection sensitivity and analysis accuracy. The analysis operation in another visual field may be repeatedly carried out until a tangible component is found. Further, the analyzer 100 may be arranged such that, in a case where no tangible component is found after presence of a tangible component is checked once or a few times in different visual fields, the analysis operation is stopped. This setting may be arbitrarily set by a user depending on the purpose.

Second Embodiment

According to First Embodiment described so far, in a case where no focus state is detected in S5 and the automatic focusing operation is ended in the process flow of FIG. 4, the procedure returns to S3 so that the analysis operation with the initial setting is carried out again in another visual field. However, the present invention is not limited to the processing operation described above. For example, the present invention may encompass such an embodiment that, in a case where no focus state is detected and automatic focusing operation is ended, an analysis in another visual field is carried out only in the vicinity of an analysis end position. The following describes one embodiment in which this processing operation is carried out. For convenience of description, to a member in the present embodiment having the same function as a member in First Embodiment, the same numeral reference as that of the corresponding member in First Embodiment is given. Further, the description of such a member is omitted in the present embodiment. The description in the present embodiment deals with differences between First Embodiment and the present embodiment.

The present embodiment deals with an analyzer having the same arrangement as that of the analyzer of First Embodiment. Therefore, the description of the arrangement of the analyzer is omitted here. S1 to S21 in a process flow of the present embodiment are same as S1 to S21 in the process flow of FIG. 4. Therefore, the following description deals with a part of the process flow of the present embodiment which part is different from that of First Embodiment. Particularly, the following description deals with S22 and subsequent steps, which are different from those in FIG. 4.

Figure 5:
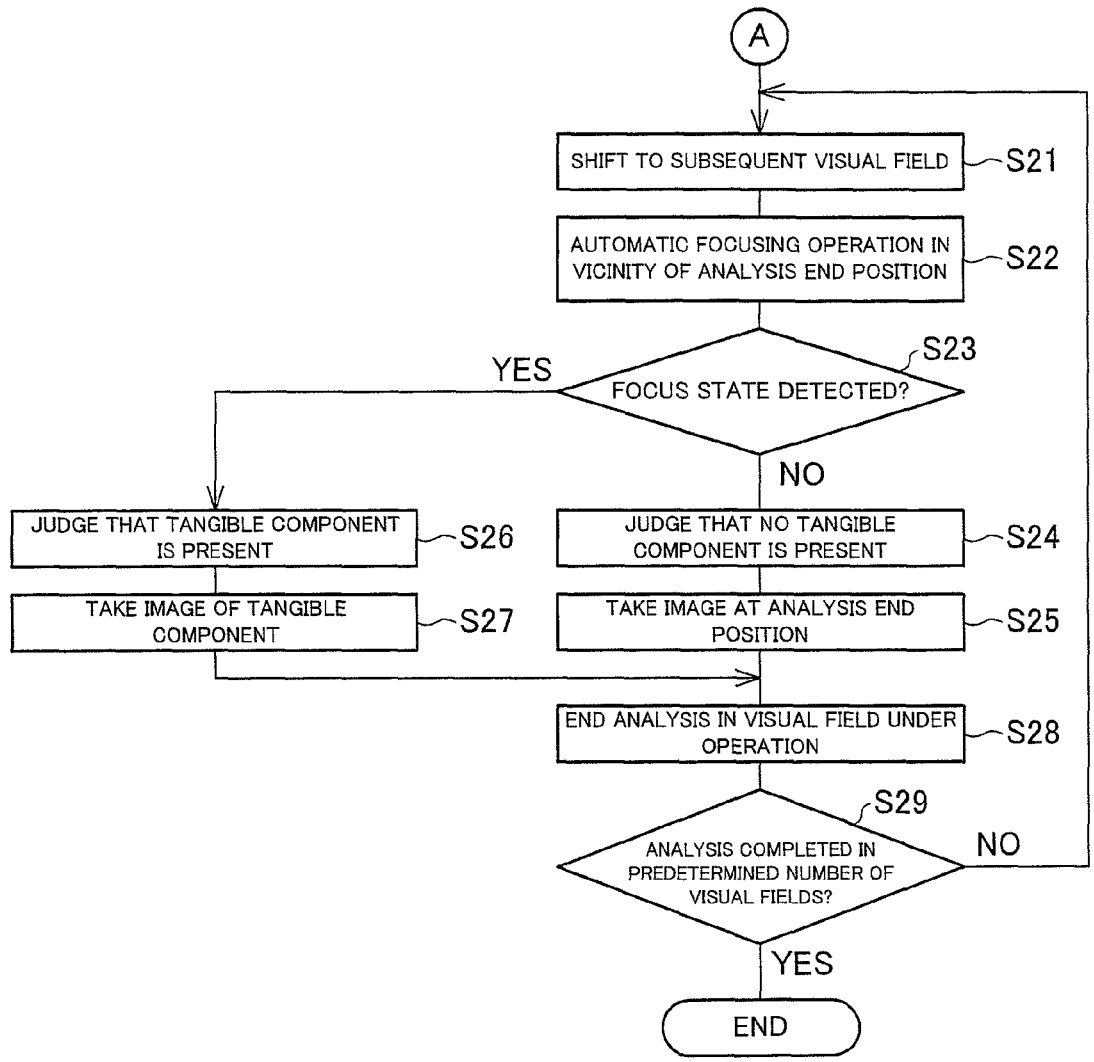
FIG. 5 is a view illustrating another example of the process flow of the analyzer according to one embodiment of the present invention.

FIG. 5 is a process flow of the analyzer according to the present embodiment, and illustrates a process flow including steps to be carried out after Arrow A, which comes out from S20 in FIG. 4. That is, in the present embodiment, S1 to S20, which are not illustrated in FIG. 5, are the same as those in FIG. 4.

That is, after the analysis operation is stopped in the preceding visual field in S20 illustrated in FIG. 4, the control section 5 controls the drive section 3 so as to shift the visual field to another visual field and to carry out an analysis therein (S21 in FIG. 5). That is, if the judgment section 6 judges, in S18, that no tangible component is present in the preceding visual field, the control section 5 controls, in S21 in FIG. 5, the automatic focusing section 4 and/or the drive section 3 so as to change, in the horizontal direction (i.e., in the x-axis and y-axis directions), the relative position between the objective lens 1 and the sample 23, for the purpose of carrying out another analysis of a tangible component in another visual field.

Next, in S22 in FIG. 5, in a case where another analysis of a tangible component is carried out in "another visual field" obtained in S21, the control section 5 controls so as to carry out automatic focusing operation only in a predetermined distance (area) in the vicinity of the analysis end position at which the automatic focusing operation in the preceding visual field is ended. That is, this process is carried out as follows: In a case where (i) an analysis is carried out in a plurality of visual fields and (ii) it is determined that no tangible component is present in a preceding visual field, an analysis in a subsequent visual field(s) following the preceding visual field is carried out only in the vicinity of an analysis end position. This is based on knowledge originally found by the inventors. The knowledge is as follows: "If no tangible component is present in a certain visual field, there is a high possibility that no tangible component is present in other visual fields either". This step eliminates need for carrying out, in a case where it is determined that no tangible component is present in a preceding visual field, the analysis operation with the initial setting for checking whether or not a tangible component is present (i.e., the operation for extensively observing an area where a tangible component is assumed to be present) in another visual field. This increases a processing speed of an analysis, thereby allowing effective analysis.

Specifically, in this process, for example, the automatic focusing operation may be carried out in a predetermined distance ahead and behind (along the z-axis) the analysis end position. The "predetermined distance" in this step may be arbitrarily set, and is not particularly limited. However, it is preferable that the "predetermined distance" is in a range from 0.5 μm to 20 μm, and more preferably in a range from 1 μm to 10 μm. This is based on the following reason.

Examples of a tangible component to be analyzed may encompass a blood cell, a fungus, and the like, in addition to an epithelium and a cast. Methods for analyzing these tangible components are slightly different from each other. For example, in a case of analyzing an epithelium and a cast, it is to some extent possible to analyze them by their features such as: an external size of a part of them; and a size of a nucleus of them. On the other hand, in a case of analyzing a red blood cell and a white blood cell, which have a relatively similar size, a classification is carried out in such a manner that (i) the red blood cell and the white blood cell are classified in accordance with their sizes, respectively, and (ii) the red blood cell and the white blood cell thus classified are further classified into finer categories by using a parameter, respectively. The parameter is, for example, staining properties of cytoplasm and roundness of a cell membrane. Therefore, it is very preferable for the analysis of a blood cell to be carried out so that the blood cell is exactly focused (because if a focus is out, an outline of the blood cell becomes blurred and thereby the blood cell bigger than an actual size is observed). A diameter of a red blood cell is approximately 8 μm, and a diameter of a white blood cell is approximately 10 μm. Therefore, in the case of analyzing the red blood cell and the white blood cell, it is preferable that a focus position (an exactly-focused position) is searched for within a distance of approximately 8 μm to 10 μm. A size of a fungus is approximately 1 μm to 3 μm. Therefore, in a case of analyzing a fungus, it is preferable that the analysis is carried out with resolution of at least approximately 1 μm. Thus, setting the "predetermined distance" in the foregoing range makes it possible to accurately judge presence of various kinds of tangible components.

In a case where no focus state is detected in S23 and the automatic focusing operation is ended, the judgment section 6 judges that no tangible component is present in the visual field under operation (S24). Then, the image pickup section 7 obtains an image of the sample 23 at a position (an analysis end position) where the automatic focusing operation is ended. After that, the procedure proceeds to S28.

On the other hand, if a focus state is detected in S23, the judgment section 6 judges that a tangible component is present (S26). Then, in S27, the image pickup section 7 takes an image of the tangible component. After that, the procedure proceeds to S28.

After the image is obtained in S25 or S27, the analysis operation is stopped in the visual field under operation in S28. After that, in S29, the control section 5 judges whether or not an analysis has been completed in a predetermined number of visual fields (e.g., a few tens of visual fields, and more preferably 50 to 100 visual fields). If it is judged that the analysis has been completed in the predetermined number of visual fields, the procedure is ended. On the other hand, if it is judged that the analysis has not been completed in the predetermined number of visual fields, the procedure returns to S21. Then, the steps (S21 to S29) for carrying out automatic focusing operation in another visual field are carried out again.

According to the analyzer 100, which carries out the foregoing analysis operation, if it is judged that no tangible component is present in a certain visual field, an analysis is carried out in the vicinity of an analysis end position. The inventors originally found knowledge such that if no tangible component is present in a certain visual field, there is a high possibility that no tangible component is present in other visual fields either. The foregoing arrangement is based on the knowledge, and does not carry out the analysis operation with the initial setting for checking whether or not a tangible component is present in another visual field. This increases a processing speed of an analysis, thereby allowing an effective analysis.

After the process flow in FIG. 4 and FIG. 5 is terminated, the analyzer 100 may output an analysis result via an output section 10.

Further, in the analyzer 100, a memory section 9 may store images of tangible components in order, and then a classifying section 8 may classify the tangible components. For example, after an image and an analysis result stored in the memory section 9 are transmitted from the memory section 9 to the classifying section 8, the classifying section 8 may carry out (i) the color extraction step for separating colors according to brightness and chromaticity based on an RGB value, (ii) the image binarization processing step including spot removal, line segment writing, and image separation, and (iii) the characteristic amount calculation step for obtaining a characteristic amount such as an area, circularity, a circle-equivalent diameter, a perimeter, an absolute maximum amount, an X/Y ratio in a Feret's diameter, an X/Y ratio in a maximum chord length, and a ratio between a short axis length and a long axis length. Then, the classifying section 8 may compare the characteristic amount thus obtained with a set value of a tangible component so as to carry out a classification, the set value having been set in advance. After that, the classifying section 8 may output, to the output section 10, the classification result and/or the image which is taken. As described above, providing the classifying section 8 to the analyzer realizes an analyzer (i.e., a tangible component classification device) which (i) obtains an image of a tangible component contained in a biological sample and (ii) automatically classifies and measures the tangible component per each kind.

Further, the present invention encompass an analyzer for taking an image of a tangible component contained in a biological sample by means of a digital camera and automatically classifying and measuring the tangible component in accordance with the image thus taken, the analyzer including: a stage on which a preparation holding the biological sample therein is placed; an objective lens provided above the stage; a digital camera provided above the objective lens; and a light source provided below the stage. In the analyzer, the stage is moved in three dimensional directions, for the purpose of automatically focusing on an image and taking such an image in a plurality of visual fields. Further, in the analyzer, the focusing operation is carried out for each preparation, and then the stage is caused to move a predetermined distance so that the automatic focusing operation is carried out.

In this arrangement, it is preferable that a focus point obtained by the focusing operation is recognized by the contrast-based type automatic focusing operation function. Further, it is preferable that the preparation includes: the biological sample; a cover glass section provided above the biological sample; and a slide glass section provided below the biological sample. Furthermore, it is preferable that the focusing operation for the preparation is carried out by focusing on a surface of the slide glass.

Further, it is preferable that the predetermined distance is equal to or shorter than a distance between the cover glass section and the slide glass section. Furthermore, it is preferable that the image is taken under a certain condition, without changing the predetermined drive distance depending on a kind or a type of a tangible component in the biological sample. Moreover, it is preferable that the image is taken under a certain condition, without exchanging the objective lens one with another depending on a kind or a type of a tangible component contained in the biological sample.

Third Embodiment

Figure 7:
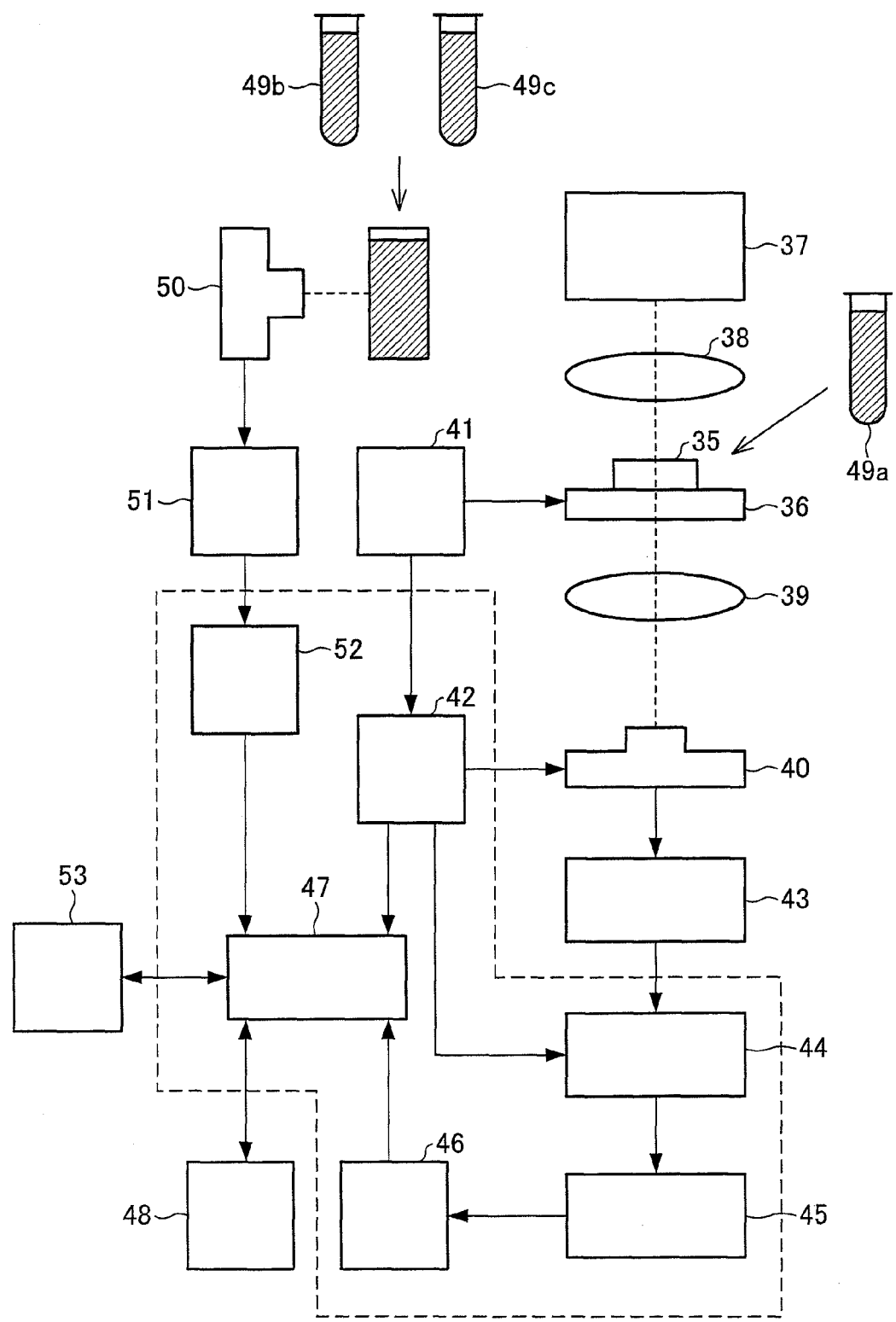
FIG. 7 is a view illustrating one example of a tangible component analyzer according to the present invention.

FIG. 7 is a view illustrating one example of a tangible component analyzer according to the present invention, and illustrates a urinary sediment component analyzer.

In the example illustrated in FIG. 7, a slide glass 35 is used as the light-transmitting plate. As illustrated in FIG. 6 (a), the slide glass 35 is integrally formed with a cover glass, that is, the slide glass 35 is arranged so as to be a slide glass integrating a cover glass. The slide glass 35 is placed on an XY table 36, which is the image pickup stage. The XY table 36 includes a step motor as a drive source. The XY table 36 is driven in accordance with a signal transmitted from a drive circuit 41 so as to change an image pickup position by freely (i) moving the slide glass 35 in the x-axis and y-axis directions and (ii) stopping moving the slide glass 35.

A CCD camera 40 with an automatic focusing function is used as the image pickup means. The CCD camera 40 is provided with an objective lens as the magnifying means. The identifying means includes an image processing control circuit 42, an image memory 44, a characteristic extraction circuit 45, an identification arithmetic circuit 46, a central control section 47, and an arithmetic circuit 52. The identifying means are surrounded by a dotted line in FIG. 7. The element with the reference numeral "53" in FIG. 7 indicates a display used as the output device. The element with the reference numeral "48" in FIG. 7 indicates an image memory device for storing a result obtained by identifying various components. Next, a process to be carried out in the analyzer of the present invention is described in time series.

Firstly, a predetermined amount of a urine sample, which is liquid to be examined, is taken from a sample container, and the urine sample thus taken is poured to three reaction tubes 49a, 49b, and 49c by means of a probe. Here, in order to take and pour the urine sample more uniformly, the urine sample is stirred before the taking and pouring. In a case of using, as the sample container, a container to which a bar code is attached in advance, a bar-code reading device reads out the bar code in advance. Reading out, from the bar code, information such as (a) whether or not a sample is stored, (b) a kind of a sample, and (c) a sample number makes it possible to easily process data and identify a sample in subsequent steps. Next, a necessary amount of a staining solution is poured into the reaction tube 49a so that a tangible component is stained. After approximately two minutes, a reaction solution obtained by the mixture of the liquid to be examined and the staining solution is taken from the reaction tube 49a, and is poured into the slide glass (slide glass 35) integrating the cover glass. Staining reaction time and a reaction temperature are arbitrarily set.

Next, in order to take an image of the liquid to be examined, light is emitted from a lamp 37, which is the light source. The light (illustrated in a dotted line) emitted from the lamp 37 proceeds along an optical axis, and goes through a condenser lens 38, thereby being collected onto the liquid to be examined which is placed on the slide glass 35. Then, the objective lens 39 forms, at an image formation position, a sample image of a tangible component in the liquid to be examined. After that, the sample image thus formed at the image formation position is projected, as an image, onto an image pickup surface of the CCD camera 40, and then the image is photoelectrically converted.

The image processing control circuit 42 controls the drive circuit 41 so as to control the movement or the stop of the XY table 36. Further, the image processing control circuit 42 causes the CCD camera 40 to take an image when the XY table 36 stops. The image thus taken by the CCD camera 40 is converted into digital image data by means of an analog-digital converter 43. The image processing control circuit 42 stores, in an image memory 44, the digital image data thus obtained.

After the image processing control circuit 42 stores the digital image data in the image memory 44, the image processing control circuit 42 moves the XY table 36 so as to change an image pickup position (visual field). Then, as well as in the above-mentioned step, an image is taken, the image is converted into digital image data (i.e., a digital-analog conversion), and the digital image data is stored in the memory. The image processing control circuit 42 repeatedly carries out a series of the steps until the series of the steps is carried out for a predetermined number of visual fields. The XY table 36's movement for changing the image pickup position may be controlled so as to be carried out after an analysis of an image has been completed in one visual field.

Next, the image processing control circuit 42 inputs the image data from the image memory 44 to the characteristic extraction circuit 45. The characteristic extraction circuit 45 extracts, from the image, a characteristic amount (e.g., an area, circularity, a circle-equivalent diameter, a perimeter, an absolute maximum length, an X/Y ratio in a Feret's diameter, an X/Y ratio in a maximum chord length, and a ratio between a short axis length and a long axis length, each of which is of a tangible component), as a primary parameter. The image processing control circuit 42 inputs, to the identification arithmetic circuit 46, (a) the primary parameter and (b) a secondary parameter obtained by carrying out combinational operation of the primary parameters.

The identification arithmetic circuit 46 classifies a tangible component by using a neural network. The neural network carries out, in advance, learning by using a large amount of data referring to a judgment made by an expert, and has an optimized coupling coefficient between neurons. The identification arithmetic circuit 46 carries out neural network operation by using the primary parameter and the secondary parameter thus inputted, so as to carry out an automatic classification of a tangible component to be analyzed. Instead of the neural network operation, the identification arithmetic circuit 46 may carry out an automatic classification of a tangible component by using a statistical learning/recognition method.

The central control section 47 causes the image memory device 48 to store the analysis result and the image data. In the present embodiment, a magneto-optical disk, which has a large memory capacity, is used as the image memory device 48.

In order to measure the amount of a microbe such as a fungus in the urine sample, a trichloroacetic acid is added to the reaction tube 49b, and a part of the sample in the reaction tube 49b is taken. Then, an ATP monitoring reagent is added to the sample thus taken so as to cause the sample to emit light. The trichloroacetic acid is not added to the reaction tube 49c, and a part of the sample in the reaction tube 49c is taken as a control. Then, as well as to the sample taken from the reaction tube 49b, the ATP monitoring reagent is added to the sample thus taken from the reaction tube 49c so as to cause the sample to emit light. The emitted light is detected by a luminometer 50. An integrator circuit 51 measures the amount of the light detected by the luminometer 50 in a predetermined period of time, and integrates the amount of the emitted light. Next, the arithmetic circuit 52 converts, into the amount of ATP, information regarding the amount of the emitted light (the number of photons) thus integrated by the integrator circuit 51, for the purpose of obtaining the amount of the microbe. This conversion is carried out in accordance with a calculation formula obtained in advance based on standard ATP. Then, the amount of the microbe thus obtained is inputted to the central control section 47.

After the classification is carried out with respect to images which are taken in visual fields, respectively, all the classification results thus obtained are integrated by the central control section 47. Then, the central control section 47 converts, into qualitative data (e.g., −, ±, +, ++, +++), (i) the integrated classification result and (ii) the amount of the microbe inputted from the arithmetic circuit 52, in accordance with a boundary value (a standard value of a tangible component) which is inputted in advance. The qualitative data thus obtained and the image data are inputted to the output device 53 such as a display and a printer.

Figure 9:
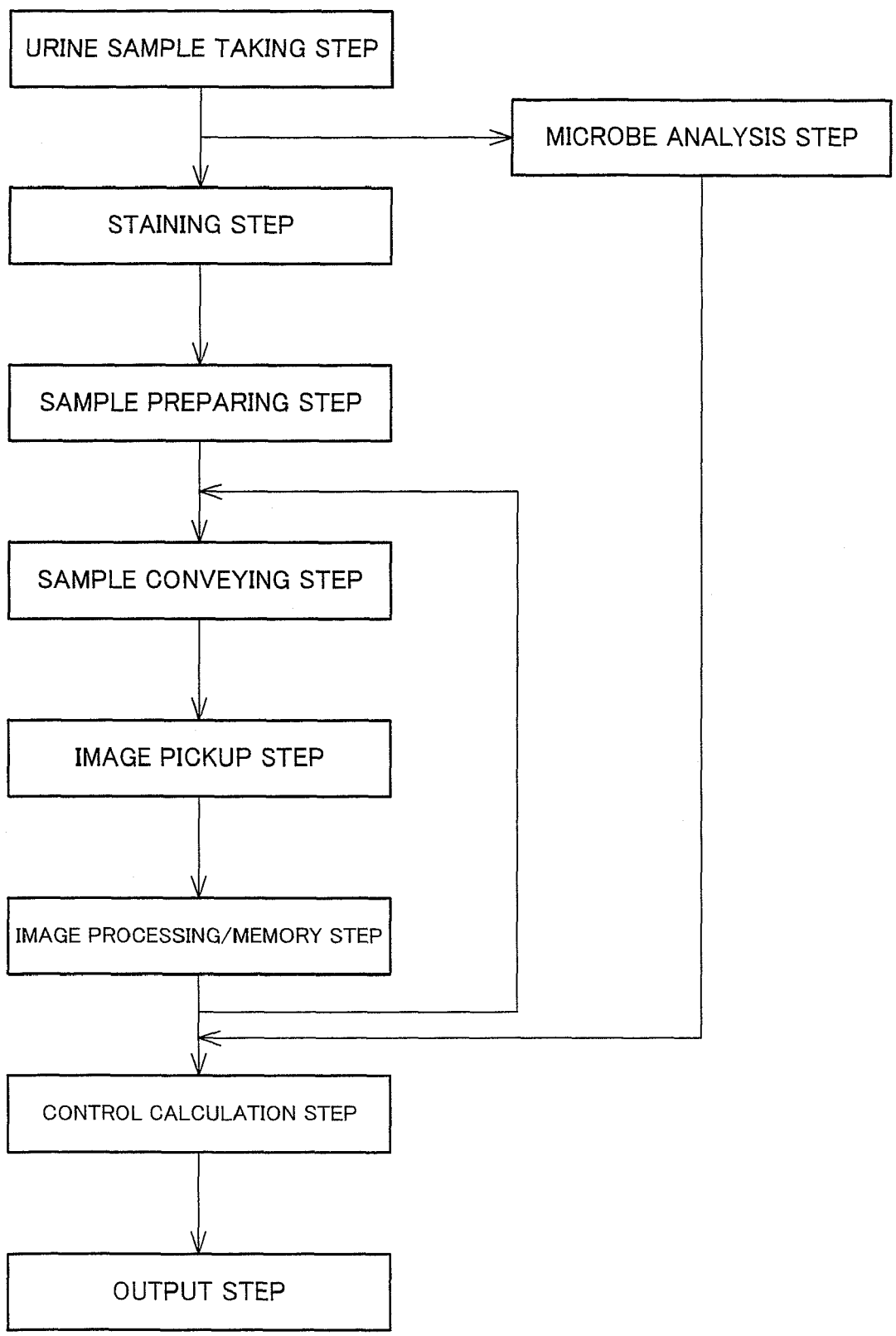
FIG. 9 is a step block chart illustrating one example of a tangible component analysis method according to the present invention.

FIG. 9 is a step block chart illustrating one example of a tangible component analysis method according to the present invention. In this process, an analysis is carried out by using the tangible component analyzer illustrated in FIG. 7. The following describes each step in FIG. 9.

[Urine Sample Taking Step]
In this step, a raw urine liquid sample 200 is stirred, and is not subjected to centrifugation. Then, each 0.75 ml of the raw urine liquid sample is taken and poured to three predetermined reaction tubes.

[Staining Step]
In this step, 0.25 ml of an S (Sternheimer) staining solution is added to one of the three reaction tubes to which the raw urine liquid sample is poured. Then, a mixture solution thus obtained is stirred therein.

[Sample Preparing Step]
This step is for placing, on a light-transmitting plate, liquid to be examined. In this step, 0.015 ml of liquid to be examined, which is the mixture solution obtained by adding the S staining solution to the sample, is taken. Then, the liquid to be examined thus taken is poured into a space in a slide glass integrating a cover glass. Thus, a sample is prepared.

[Sample Conveying Step]
In this step, the sample thus prepared is set on an image pickup stage, and is conveyed to an image pickup position.

[Image Pickup Step]
This step includes (i) a step for magnifying a sample image of a tangible component in liquid to be examined and (ii) a step for automatically focusing on the sample image of the tangible component thus magnified and taking the sample image of the tangible component. In this step, firstly, an objective lens (magnifying means) provided to a CCD camera magnifies the sample image. Next, the CCD camera, which is set toward the image pickup stage, automatically focuses on the sample image, and takes the sample image which is magnified.

[Image Processing/Memory Step]

This step is for identifying a component in an image by processing the image which is taken. In this step, firstly, the image which is taken is stored in a magneto-optical disk. Next, various tangible components in the sample are classified into corresponding categories, respectively, in accordance with the image data thus stored. The classification is carried out by using, for example, an arithmetic circuit including a function for learning and recognizing earlier data. Then, the number of each component is counted up. The result obtained by the classification and the counting is transmitted to a control calculation step. Note that the foregoing image pickup step and the image processing/memory step are repeatedly carried out until these steps are carried out for 100 visual fields, while the image pickup stage is moved so as to change the image pickup position.

[Microbe Amount Analysis Step]

This step is for working out the amount of a tangible component in accordance with an optical characteristic amount derived from the tangible component. In this step, firstly, 0.75 ml of a 0.4% trichloroacetic acid is added to another one of the three reaction tubes to which the urine sample is poured in the urine sample pick-up step. Nothing is added to the other one of the three reaction tubes so that this reaction tube is set as a control. Each 0.01 ml of the urine sample is taken from the reaction tubes. Then, to each of the urine samples thus taken, 0.5 ml of an ATP monitoring reagent (including: 30 mM glycylglycine buffer (pH 7.8); 5 mM magnesium sulfate; 0.1 mM luciferin sulfate; and 10 U/ml of luciferase) is added so that the urine samples emit light. The emitted light is detected by a luminometer. Then, an integrator circuit or the like measures the amount of the emitted light, and integrates the amount of the emitted light thus measured.

Figure 11:
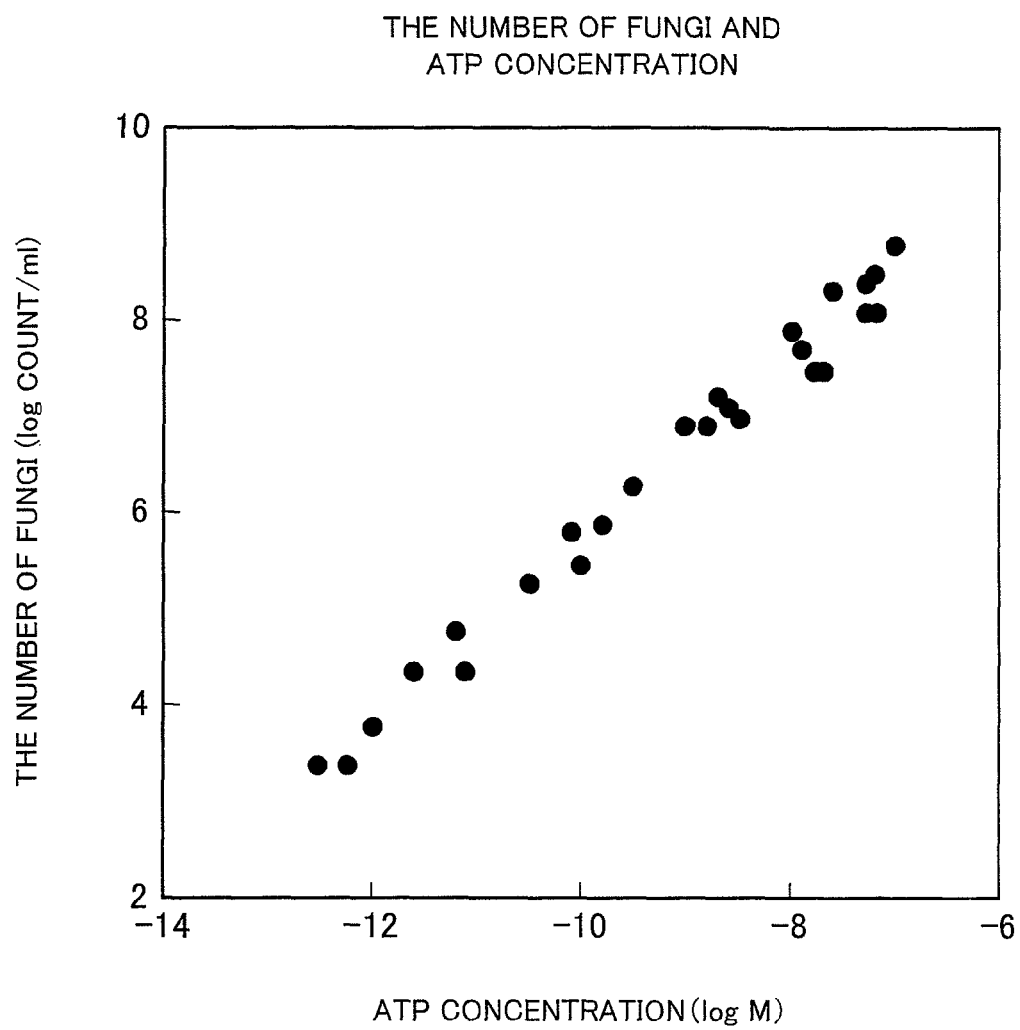
FIG. 11 is a correlation diagram between an ATP concentration and the number of fungi in urine.

Next, the amount of ATP in each of the samples is worked out in accordance with a calculation formula obtained in advance based on standard ATP. After that, the remainder between (a) the amount of ATP in the sample to which the trichloroacetic acid is added and (b) the amount of ATP in the sample which is set as the control is worked out. Thus, the amount of ATP, which is derived from the microbe in the sample, is obtained. The result thus obtained is transmitted to the control calculation step. FIG. 11 illustrates a correlation diagram between an ATP concentration in urine and the number of fungi.

[Control Calculation Step]

In this step, the results obtained by the image processing/memory step and the microbe amount analysis step are integrated, so as to be outputted to a display, a printer, or the like. Table 1 shows one example of the output (printing).

TABLE 1

|  | Sample No. | | | |
| --- | --- | --- | --- | --- |
|  | 1 | 2 | ... | 200 |
| White Blood Cell | ± | ± | ... | + |
| Red Blood Cell | + | + | ... | + |
| Epithelial Cell | − | ± | ... | + |
| Cast | ± | + | ... | ± |
| Fungi | + | − | ... | ± |

Table 2 shows a matching rate with respect to the analysis result obtained by the image processing in this embodiment. That is, it is checked whether or not a component name (e.g., a white blood cell and a red blood cell) determined by a classification and an analysis in the image processing matches a component name judged by a person. The person makes the judgment by observing, with his/her eyes, images which are taken.

TABLE 2

| Tangible Component | White Blood Cell | Red Blood Cell | Epithelial Cell | Cast | Fungi |
| --- | --- | --- | --- | --- | --- |
| Matching Rate to Image Observation | 88.9% | 90.3% | 78% | 90% | 80% |

Fourth Embodiment

Figure 8:
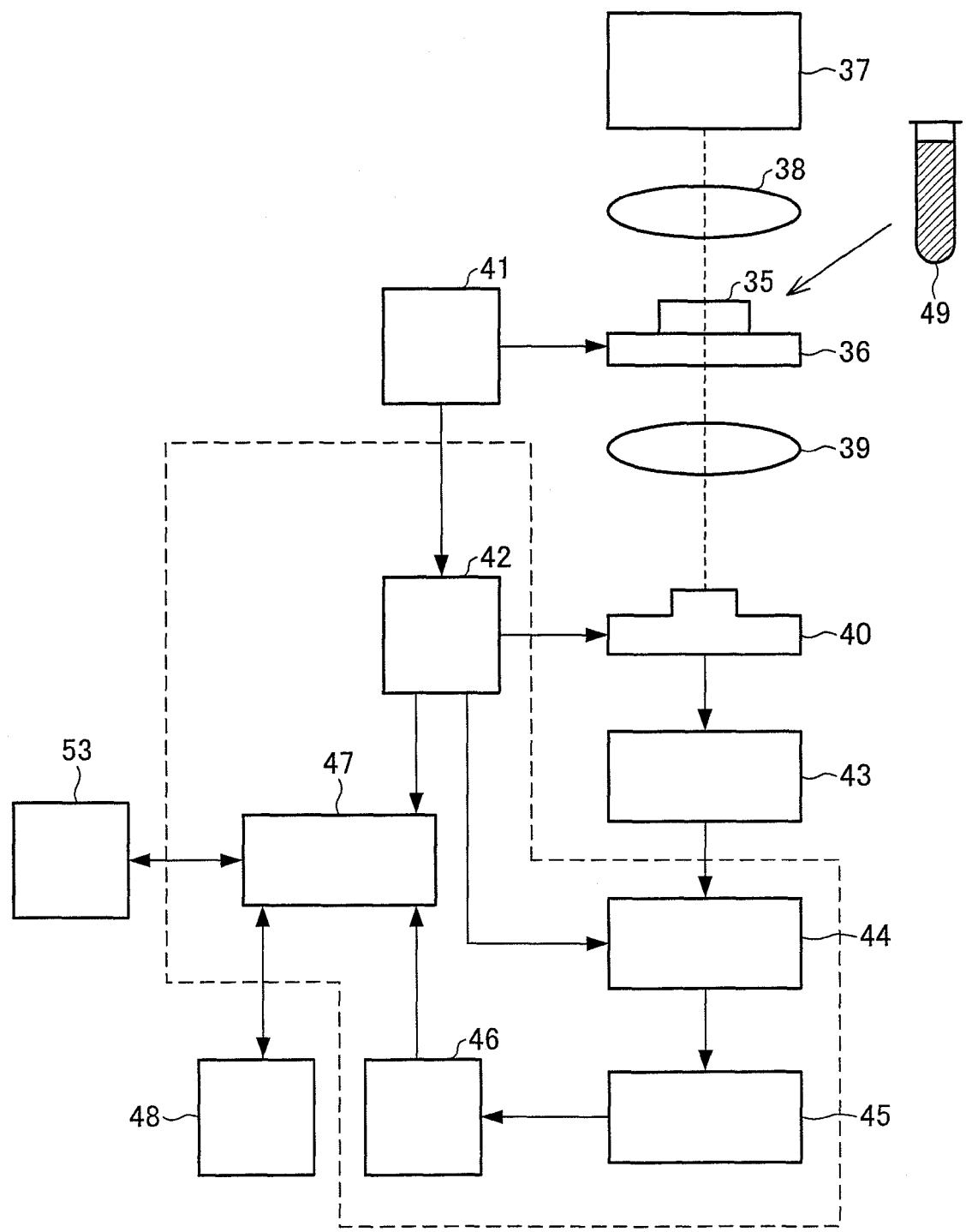
FIG. 8 is a view illustrating another example of the tangible component analyzer according to the present invention.

FIG. 8 is a view illustrating another example of the tangible component analyzer according to the present invention. Unlike the example illustrated in FIG. 7, the example illustrated in FIG. 8 does not include the step for adding the ATP monitoring reagent. Therefore, the example illustrated in FIG. 8 is not provided with the luminometer, the integrator circuit, and the arithmetic circuit, each of which is used in the example illustrated in FIG. 7. Accordingly, as illustrated in the example in FIG. 8, a necessary amount of a urine sample is taken and poured only to a reaction tube 49. Except for this point, the example illustrated in FIG. 8 has the same arrangement as that of the example illustrated in FIG. 7.

Figure 10:
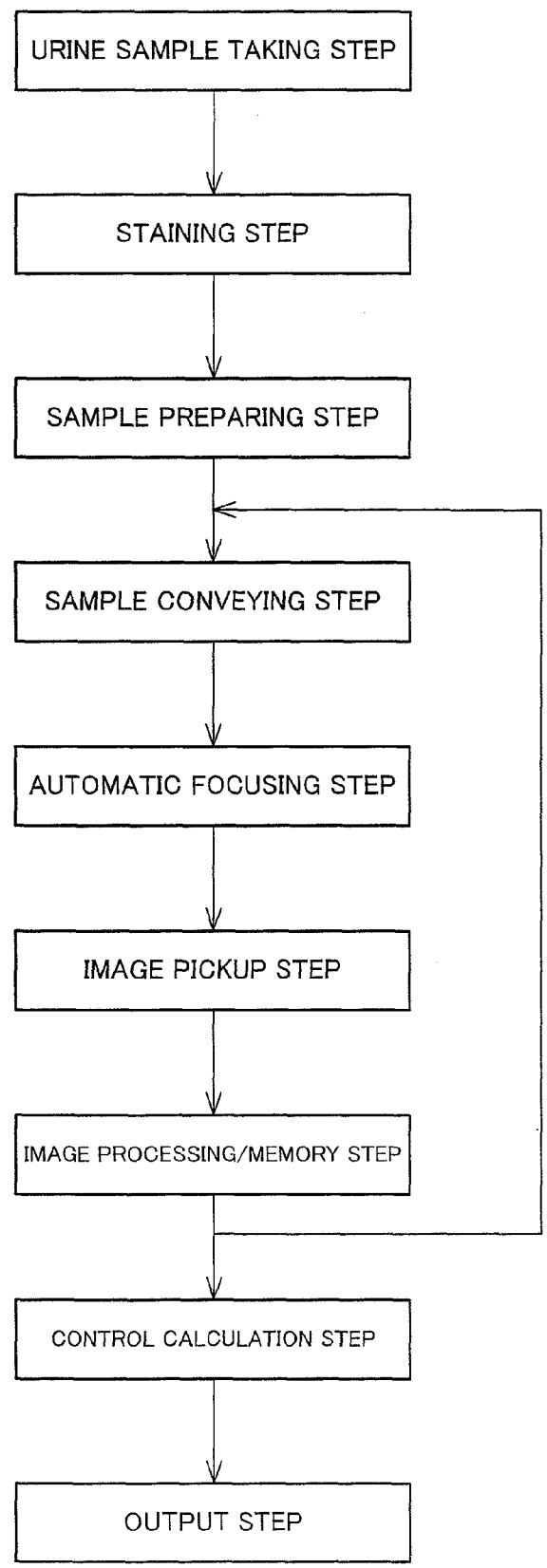
FIG. 10 is a step block chart illustrating another example of the tangible component analysis method according to the present invention.

FIG. 10 is a step block chart illustrating another example of the tangible component analysis method according to the present invention. In this tangible component analysis method, an analysis is carried out by using the analyzer illustrated in FIG. 8. The following describes each step in FIG. 10.

[Urine Sample Taking Step]

In this step, a raw urine liquid sample is stirred, and is not subjected to centrifugation. Then, 0.75 ml of the raw urine liquid sample is poured to a reaction tube.

[Staining Step]

In this step, 0.25 ml of an S (Sternheimer) staining solution is added to the reaction tube to which the raw urine liquid sample is poured. Then, a mixture solution thus obtained is stirred therein.

[Sample Preparing Step]

In this step, as well as in the example illustrated in FIG. 9, 0.015 ml of the mixture solution, to which the S staining solution is added, is taken. Then, the mixture solution thus taken is poured into a space in a slide glass integrating a cover glass. Thus, a sample is prepared.

[Sample Conveying Step]

In this step, as well as in the example illustrated in FIG. 9, the sample thus prepared is set on an image pickup stage, and is conveyed to an image pickup position.

[Image Pickup Step]

In this step, as well as in the example illustrated in FIG. 9, a sample image of a tangible component is magnified and is automatically focused. Then, a CCD camera, which is set toward the image pickup stage, takes the sample image thus magnified.

[Image Processing/Memory Step]

In this step, as well as in the example illustrated in FIG. 9, (i) the image thus taken is stored, (ii) various tangible components in the sample are classified into corresponding categories, respectively, in accordance with the image data thus stored, and (iii) the number of each component is counted up. The result obtained by the classification and the counting is transmitted to a control calculation step. Note that the image pickup step and the image processing/memory step are repeatedly carried out until these steps are carried out for 100 visual fields, while the image pickup stage is moved so as to change the image pickup position.

[Control Calculation Step]

In this step, the results obtained by the image processing/memory step are integrated, so as to be outputted to a display, a printer, or the like. Table 3 shows one example of the output (printing). In Table 3, a result obtained in a high power field (HPF) is indicated by a symbol.

TABLE 3

| | Sample No. | | | |
|---|---|---|---|---|
| | 1 | 2 | ... | 200 |
| White Blood Cell | 1 to 4/HPF | Below 1/HPF | ... | 5 to 9/HPF |
| Red Blood Cell | 5 to 9/HPF | 5 to 9/HPF | ... | Below 1/HPF |
| Epithelial Cell | Below 1/HPF | 1 to 4/HPF | ... | 5 to 9/HPF |
| Cast | − | + | ... | + |
| Fungi | + | − | ... | ± |

The present invention is not limited to the description of the embodiments above, but may be altered by a skilled person within the scope of the claims. An embodiment based on a proper combination of technical means disclosed in different embodiments is encompassed in the technical scope of the present invention.

Lastly, the blocks of the analyzer 100 (particularly, the focus state detecting section 2, the automatic focusing section 4, the control section 5, the judgment section 6, and the classification section 8) may be realized by way of hardware or software as executed by a CPU as follows:

The analyzer 100 includes a CPU (central processing unit) and memory devices (memory media). The CPU (central processing unit) executes instructions in control programs realizing the functions. The memory devices include a ROM (read only memory) which contains programs, a RAM (random access memory) to which the programs are loaded, and a memory containing the programs and various data. The objective of the present invention can also be achieved by mounting to the analyzer 100 a computer-readable storage medium containing control program code (executable program, intermediate code program, or source program) for the analyzer 100, which is software realizing the aforementioned functions, in order for the computer (or CPU, MPU) to retrieve and execute the program code contained in the storage medium.

The storage medium may be, for example, a tape, such as a magnetic tape or a cassette tape; a magnetic disk, such as a Floppy (Registered Trademark) disk or a hard disk, or an optical disk, such as CD-ROM/MO/MD/DVD/CD-R; a card, such as an IC card (memory card) or an optical card; or a semiconductor memory, such as a mask ROM/EPROM/EEPROM/flash ROM.

The analyzer 100 may be arranged to be connectable to a communications network so that the program code may be delivered over the communications network. The communications network is not limited in any particular manner, and may be, for example, the Internet, an intranet, extranet, LAN, ISDN, VAN, CATV communications network, virtual dedicated network (virtual private network), telephone line network, mobile communications network, or satellite communications network. The transfer medium which makes up the communications network is not limited in any particular manner, and may be, for example, wired line, such as IEEE 1394, USB, electric power line, cable TV line, telephone line, or ADSL line; or wireless, such as infrared radiation (IrDA, remote control), Bluetooth (Registered Trademark), 802.11 wireless, HDR, mobile telephone network, satellite line, or terrestrial digital network. The present invention encompasses a carrier wave or data signal transmission in which the program code is embodied electronically.

An analyzer according to the present invention has the foregoing arrangement. Therefore, the analyzer is capable of judging whether or not a tangible component is present in a sample in a preparation. Further, if the tangible component is judged to be present, the analyzer is capable of carrying out an analysis of the tangible component with efficiency and high accuracy. Note that the sample may be either of a biological sample or a non-biological sample.

Further, in the analyzer according to the present invention, it is preferable that: if the focus state detecting means does not detect the focus state and the automatic focusing operation is ended, the judgment means judges that no tangible component is present in the visual field under operation; if the judgment means judges that no tangible component is present in the visual field under operation, the control means controls the automatic focusing means and/or the drive means so as to change, in the horizontal direction, the relative position between the objective lens and the sample, for the purpose of carrying out said another analysis of the tangible component in said another visual field; and in the case where said another analysis of the tangible component is carried out in said another visual field, the control means controls again the automatic focusing means and/or the drive means so as to carry out the automatic focusing operation in the range from the predetermined analysis start position to the preset analysis end position, the predetermined analysis start position being between the light-transmitting plate and the light-transmitting covering plate (in a vertical direction).

With this arrangement, when it is determined that no tangible component is present in a certain visual field, the analysis operation with the initial setting (i.e., the operation for extensively observing an area where a tangible component is assumed to be present) is carried out again so as to check whether or not a tangible component is present in another visual field. This increases a possibility of finding a tangible component, thereby improving detection sensitivity and analysis accuracy. The analysis operation in another visual field may be arranged such that the analysis operation with the initial setting is repeatedly carried out until it is judged that a tangible component is present. Further, instead of this arrangement, the analysis operation in another visual field may be arranged such that (i) it is confirmed, once or a few times, whether or not a tangible component is present in another visual field and (ii) if no tangible component is found, the analysis operation with the initial setting is stopped.

Furthermore, in the analyzer according to the present invention, it is preferable that: if the focus state detecting means does not detect the focus state and the automatic focusing operation is ended, the judgment means judges that no tangible component is present in the visual field under operation; if the judgment means judges that no tangible component is present in the visual field under operation, the control means controls the automatic focusing means and/or the drive means so as to change, in the horizontal direction, the relative position between the objective lens and the sample, for the purpose of carrying out said another analysis of the tangible component in said another visual field; and in the case where said another analysis of the tangible component is carried out in said another visual field, the control means carries out the operation for carrying out the automatic focusing operation in the predetermined distance in the vicinity of the analysis end position at which the automatic focusing operation is ended.

With this arrangement, when it is determined that no tangible component is present in a certain visual field, an analysis is carried out in the vicinity of the analysis end position. The inventors have originally found the following knowledge: "If no tangible component is present in a certain visual field, there is a high possibility that no tangible component is present in other visual fields either". The above-mentioned arrangement is based on this knowledge, and does not carry out the analysis operation with the initial setting for checking whether or not a tangible component is present in another visual field. This increases a processing speed of an analysis, thereby allowing an effective analysis.

Moreover, in the analyzer according to the present invention, it is preferable that the control means sets, as the predetermined analysis start position, a position to which the objective lens is moved, by means of offset movement of a predetermined distance, from a position where the objective lens is focused on the light-transmitting plate or the light-transmitting covering plate.

As described above, there has been the problem caused by the manufacturing allowance of the light-transmitting plate and the light-transmitting covering plate included in the preparation. The problem is caused as follows: (i) The manufacturing allowance causes differences in thicknesses of the light-transmitting plates and the light-transmitting covering plates; (ii) such the differences in thickness cause a difference in focus point between preparations, thereby preventing accurate automatic focusing operation for the preparations. However, the above-mentioned arrangement enables to set of a drive start point (i.e., a so-called zero-point calibration) in such a manner that the focusing operation for focusing the objective lens on the preparation is carried out for each preparation (i.e., the light-transmitting plate or the light-transmitting covering plate). This prevents a difference in depth of a focus point which difference is caused by the manufacturing allowance of the preparation. Further, according to the above-mentioned arrangement, after the drive start point is set, the distance between the objective lens and the sample is moved the predetermined distance by means of the offset movement. With this offset movement, it is possible to arbitrarily set the analysis start position at which the analysis is started. For example, in a case where a tangible component having a low specific gravity is to be analyzed, the following procedure may be carried out: (i) the focusing operation is carried out for each preparation; (ii) the objective lens is moved, by means of the offset movement, to the vicinity of the cover glass positioned above the preparation; and (iii) the analysis operation is carried out downward toward the slide glass. With this arrangement, it is possible to solve the problem caused by the manufacturing allowance of the preparation, thereby allowing an effective and highly-accurate analysis in a desired area.

Further, it is preferable that the analyzer according to the present invention further includes image pickup means for obtaining an image of the tangible component present in the focus position, if the judgment means judges that the tangible component is present.

With this arrangement, it is possible to obtain a clear and well-focused image of the tangible component which has been found. Therefore, it is possible to carry out a process (such as a classification and a measurement) for the tangible component, by using such the image.

Furthermore, in the analyzer according to the present invention, it is preferable that if the judgment means judges that no tangible component is present in the visual field under operation, the image pickup means obtains an image of the sample at the analysis end position at which the automatic focusing operation is ended.

With this arrangement, if no tangible component is present in the visual field in which an analysis has been carried out, it is possible to obtain an image for indicating a result that no tangible component exists in the visual field. The image thus obtained may be useful material which is used later for confirming again whether or not a tangible component is present.

Moreover, it is preferable that the analyzer according to the present invention further includes classification means for classifying the tangible component in accordance with the image thus obtained.

With this arrangement, it is possible to automatically classify the tangible component by using a characteristic amount with respect to a form (such as a color and a shape), the characteristic amount being obtained from the image. This reduces burden on a medical technologist or the like, thereby making it possible to carry out an examination effectively.

Further, it is preferable that the analyzer according to the present invention further includes output means for (i) preparing a combined image by overlapping with each other a desired number of the images thus obtained and (ii) displaying and outputting the combined image thus prepared.

With this arrangement, even in a case where the number of tangible components included in one image is small, overlapping images with each other makes it possible to see a number of tangible components in one glance.

Furthermore, it is preferable that the analyzer according to the present invention further includes output means for (i) arranging in matrix (a) the images thus obtained or (b) combined images prepared by overlapping with each other a desired number of the images thus obtained so that the images or the combined images are seen as a list screen and (ii) displaying and outputting the images or the combined images thus arranged.

With this arrangement, in a case where a user wants to see a certain component, it is possible for the user to instantly find an image including the certain component.

Moreover, it is preferable that the analyzer according to the present invention includes: identifying means for identifying the tangible component in the image by processing the image obtained by the image pickup means, the identifying means including: a function for working out an analysis result based on all identification results obtained in a predetermined number of the visual fields; and a function for outputting the analysis result via an output device.

With this arrangement, it is possible to carry out, in a totally-automated manner, the steps for (i) taking images of a number of visual fields, (ii) identifying a tangible component existing in the visual fields, and (iii) carrying out a calculation.

Further, in the analyzer according to the present invention, it is preferable that the identifying means includes a learning function in order to facilitate recognition.

Providing the learning function to the identifying means improves identification performance, thereby making it possible to carry out an identification more accurately.

Further, in the analyzer according to the present invention, it is preferable that the identifying means learns a range setting of a characteristic amount of the tangible component so as to carry out the identification by utilizing the range setting.

Furthermore, in the analyzer according to the present invention, it is preferable that the identifying means includes a function for working out an amount of the tangible component in accordance with an optical characteristic amount derived from the tangible component.

Moreover, in the analyzer of the present invention, it is preferable that the optical characteristic amount is a characteristic amount of the image, the characteristic amount being obtained by carrying out (i) color extraction in which colors are separated according to brightness and chromaticity based on red, green, and blue and (ii) image binarization processing including spot removal, line segment writing, and image separation.

Moreover, in the analyzer according to the present invention, it is preferable that the optical characteristic amount is an amount of emitted light caused by an ATP monitoring reagent.

With this arrangement, it is possible to detect even a small microbe (tangible component) that might be missed.

Further, it is preferable that the analyzer according to the present invention further includes adding means for adding, to the sample, a reagent for facilitating the identification of the various components.

This arrangement improves the optical characteristic amount, thereby decreasing a risk that the tangible component is missed or that the tangible component is misjudged. This makes it possible to carry out an identification more accurately.

Further, it is preferable that the reagent for facilitating the identification of the various components includes at least one component contained in at least one of: a Sternheimer-Malbin staining method; a Sternheimer staining method; a Prescott-Brodie staining method; a Behre-Muhlberg staining method; a Sudan III staining method; a Lugol staining method; a hemosiderin staining method; a Papanicolaou staining method; a 4-chloro-1-naphthol method; a Field staining method; a Quaglino-Flemans method; a Kaplow method; a Sato-Sekiya method; a Berlin blue method; a Giemsa staining method; a Wright staining method; a Pappenheim staining method; a Congo red staining method; a methylgreen-pyronin staining method; an alcian blue staining method; a Shorr staining method; a Feulgen staining method; an oil red O staining method; a Brecker method; a Heinz body staining method; a neutral red-Janus green supervital staining method; and a brilliant cresyl blue staining method.

With this arrangement, it is possible to combine strong points of the staining reagents, or to improve or supplement a weak point of one of the staining reagents by using another one of the staining reagents. This makes it possible to carry out a staining with higher performance.

Furthermore, in the analyzer according to the present invention, it is preferable that the objective lens has two or more magnification scales.

With this arrangement, even in a case where sizes of tangible components to be analyzed are widely distributed, it is possible to take images of the tangible components with appropriate magnification scales, respectively. This makes it possible to carry out the identification while reducing a risk that a tangible component is missed or a tangible component is misjudged.

Further, the sample that the analyzer according to the present invention analyzes may be urine, blood, serum, blood plasma, spinal fluid, semen, prostatic fluid, synovial fluid, pleural effusion, or ascites.

In a case where urine is analyzed as the sample, the urine may preferably be raw urine, concentrated urine, or a urinary sediment resulting from centrifugation of urine.

Further, in the analyzer according to the present invention, it is preferable that the light-transmitting plate is a slide glass.

Furthermore, in the analyzer according to the present invention, it is preferable that the light-transmitting plate is integrally formed with the light-transmitting covering plate for covering the sample.

With this arrangement, it is possible to significantly save in labor in a troublesome preparation preparing step.

Further, in the analyzer according to the present invention, it is preferable that at least one of the light-transmitting plate and the light-transmitting covering plate is made of: glass; plastic; glass subjected to a physical and chemical process; or plastic subjected to a physical and chemical process.

Furthermore, it is preferable that the physical and chemical process is (i) a processing method for applying, in advance, a surfactant and/or the like onto a surface of the glass or the plastic which surface contacts liquid to be examined, (ii) a plasma discharge treatment, or (iii) a corona discharge treatment.

By using the processing method, it is possible to easily give a hydrophilic property to the material.

Further, in the analyzer according to the present invention, it is preferable that: the light-transmitting plate is a multifunctional observation plate including a plate member having (i) an observation section on one side of the plate member and (ii) one or more recessed sections at a position on the one side of the plate member, the position being not the position where the observation section is provided; the observation section of the multifunctional observation plate is formed by placing, on the plate member, a sheet member having a light-transmitting property; and at least a part of the plate member which part is capable of having the sheet member thereon is made of a light-transmitting material so as to allow light to be transmitted from one side of the part to another side of the part.

Furthermore, in the analyzer according to the present invention, it is preferable that the plate member of the multifunctional observation plate is made of the light-transmitting material only.

Moreover, in the analyzer according to the present invention, it is preferable that at least one of the one or more recessed sections of the multifunctional observation plate is a heating vessel for heating the sample.

Moreover, in the analyzer according to the present invention, it is preferable that at least one of the one or more recessed sections of the multifunctional observation plate is a reaction vessel in which the liquid to be examined and the reagent are reacted with each other so that the sample is obtained.

With this arrangement, it is not necessary to additionally provide a vessel to the analyzer as in a conventional analyzer. This allows the analyzer to attain an effect such as reduction in space. Further, the vessel is provided per liquid to be observed which is placed on the observation section. This eliminates need for the cleaning, thereby preventing a measurement error caused by insufficient cleaning.

Further, in the analyzer according to the present invention, it is preferable that at least one of the one or more recessed sections of the multifunctional observation plate is a reagent vessel for storing the reagent.

The reagent vessel stores a necessary amount of at least one of the reagents required in a case where liquid to be observed (sample) is prepared by reaction between the reagent and liquid to be examined. This allows to carry out an analysis of a tangible component smoothly. Further, this can avoid such an uneconomical situation that when the remaining amount of the reagent is decreased, a new reagent is purchased and a part of the reagent which is not used at that time is left over.

Further, in the analyzer according to the present invention, it is preferable that the light-transmitting plate further includes a cleaning fluid vessel for storing a cleaning fluid for cleaning a tool for conveying the sample to the observation section.

With this arrangement, it is possible to clean, on the plate, the tool (e.g., a probe and a tip) for conveying the liquid to be observed from the heating vessel or the reaction vessel to the observation section. This makes it possible to carry out an analysis more smoothly. Further, this arrangement eliminates need for additionally providing a cleaning vessel, thereby allowing a tangible component analyzer to attain an effect such as further reduction in space.

Further, in the analyzer according to the present invention, it is preferable that the light-transmitting plate further includes a waste liquid vessel for storing the cleaning fluid which has been used for cleaning the tool.

This arrangement eliminates need for providing a waste liquid vessel to the analyzer. This allows the analyzer to attain an effect such as reduction in space, weight, and cost, compared with a conventional analyzer.

Further, in the analyzer according to the present invention, it is preferable that a part of a periphery of the sheet member having the light-transmitting property is bonded to the plate member.

Furthermore, in the analyzer according to the present invention, it is preferable that the one or more recessed sections are sealed with a sealing member.

Moreover, in the analyzer according to the present invention, it is preferable that the cleaning fluid vessel is sealed with a sealing member.

Sealing the recessed section and/or the cleaning fluid vessel with the sealing member eliminates a risk that liquid leaks out of the recessed section and/or the cleaning fluid vessel due to vibrations or the like. Further, this arrangement makes it possible to easily open the recessed section and/or the cleaning fluid vessel by: (i) breaking through the sealing member by means of the probe, when the recessed section and/or the cleaning fluid vessel is to be used; or (ii) using a jig for making a hole, immediately before the recessed section and/or the cleaning fluid vessel is used.

Further, in the analyzer according to the present invention, it is preferable that the automatic focusing means carries out the automatic focusing operation by using a contrast-based type automatic focusing operation function.

With this arrangement, it is possible to carry out the automatic focusing operation accurately. This makes it possible to carry out, in a clear manner, an analysis of a tangible component, from large one to small one.

The analyzer may be realized by a computer. In this case, the present invention may encompass: (i) an analysis program for causing a computer to function as each means so as to realize the analyzer by the computer; and (ii) a computer-readable storage medium in which the analysis program is stored.

That is, the analysis program according to the present invention is a program for operating the analyzer, and for causing a computer to function as each means. Further, the present invention encompasses the computer-readable storage medium in which the analysis program is stored.

An analysis method according to the present invention is arranged so as to include the steps of: carrying out automatic focusing operation in a range from a predetermined analysis start position to a preset analysis end position, the predetermined analysis start position being between the light-transmitting plate and the light-transmitting covering plate; judging whether or not a tangible component is present, wherein if a focus state is detected in the step for carrying out the automatic focusing operation, it is judged that a tangible component is present in a focus position at which the focus state is obtained; if it is judged that the tangible component is present in the judgment step, stopping the automatic focusing operation at the focus position at which the tangible component is judged to be present, and changing, in a horizontal direction, a relative position between the objective lens and the sample so as to carry out another analysis of a tangible component in another visual field; and carrying out, in said another analysis of the tangible component in said another visual field, the automatic focusing operation in a predetermined distance in the vicinity of the focus position at which the tangible component is judged to be present, the predetermined distance being in a vertical direction.

Therefore, it is possible to judge whether or not a tangible component is present in the sample in the preparation. Further, if the tangible component is present, it is possible to carry out an analysis of the tangible component with efficiency and high accuracy.

Further, it is preferable that the analysis method according to the present invention includes the steps of: placing the sample on the light-transmitting plate; magnifying a sample image of the tangible component contained in the sample; taking the sample image by automatically focusing on the sample image of the tangible component; and identifying the tangible component in the image by processing the image thus taken.

Furthermore, in the analysis method according to the present invention, it is preferable that (i) the steps from the step of magnifying to the step of taking the sample image or (ii) the steps from the step of magnifying to the step of identifying are repeatedly carried out until the steps are carried out for a preset number of the visual fields, while a position where the image is taken is changed.

Moreover, in the analysis method according to the present invention, it is preferable that (i) the steps from the step of placing to the step of identifying or (ii) the steps from the step of magnifying to the step of identifying are carried out in a totally-automated manner.

The present invention may incorporate the contents of Japanese Unexamined Patent Application Publication, Tokukaihei, No. 10-185803 (published on Jul. 14, 1998) and Japanese Unexamined Patent Application Publication, Tokukai, No. 2000-35384 (published on Feb. 2, 2000).

INDUSTRIAL APPLICABILITY

As described above, the present invention using a unique automatic focusing function makes it possible to carry out, with high efficiency and high accuracy, an analysis of a tangible component contained in various kinds and types of samples. Therefore, the present invention has a wide range of industrial applicability. For example, the present invention may be applied to a field such as for medicine, food, and environmental technologies, as well as in the medical field such as for medical devices and diagnostic devices.

The invention claimed is:

1. An analyzer for analyzing a tangible component contained in a sample held between a light-transmitting plate and a light-transmitting covering plate, the analyzer comprising:
   an objective lens for observing the sample;
   focus state detecting means for detecting a focus state of the objective lens;
   drive means for changing, in three dimensional directions, a relative position between the objective lens and the sample;
   automatic focusing means for controlling the drive means in accordance with a detection result obtained by the focus state detecting means, so as to perform automatic focusing operation to automatically focus the objective lens;

control means for controlling the automatic focusing means and/or the drive means so as to carry out the automatic focusing operation in a range from a predetermined analysis start position to a preset analysis end position, the predetermined analysis start position being between the light-transmitting plate and the light-transmitting covering plate; and judgment means for judging that, when the focus state detecting means detects the focus state in the automatic focusing operation, the tangible component is present in a focus position at which the focus state is obtained, if the judgment means judges that the tangible component is present, the control means controlling the automatic focusing means and/or the drive means so as to stop the automatic focusing operation at the focus position at which the tangible component is judged to be present, and changing, in a horizontal direction, the relative position between the objective lens and the sample so that another analysis of a tangible component is carried out in another visual field, and in a case where said another analysis of the tangible component is carried out in said another visual field, the control means carrying out the automatic focusing operation in a predetermined distance in the vicinity of the focus position at which, in the analysis carried out before said another analysis, the tangible component is judged to be present, the predetermined distance being in a vertical direction.

2. The analyzer as set forth in claim 1, wherein:

if the focus state detecting means does not detect the focus state and the automatic focusing operation is ended, the judgment means judges that no tangible component is present in the visual field under operation;

if the judgment means judges that no tangible component is present in the visual field under operation, the control means controls the automatic focusing means and/or the drive means so as to change, in the horizontal direction, the relative position between the objective lens and the sample, for the purpose of carrying out said another analysis of the tangible component in said another visual field; and in the case where said another analysis of the tangible component is carried out in said another visual field, the control means controls again the automatic focusing means and/or the drive means so as to carry out the automatic focusing operation in the range from the predetermined analysis start position to the preset analysis end position, the predetermined analysis start position being between the light-transmitting plate and the light-transmitting covering plate.

3. The analyzer as set forth in claim 1, wherein:

if the focus state detecting means does not detect the focus state and the automatic focusing operation is ended, the judgment means judges that no tangible component is present in the visual field under operation;

if the judgment means judges that no tangible component is present in the visual field under operation, the control means controls the automatic focusing means and/or the drive means so as to change, in the horizontal direction, the relative position between the objective lens and the sample, for the purpose of carrying out said another analysis of the tangible component in said another visual field; and in the case where said another analysis of the tangible component is carried out in said another visual field, the control means carries out the operation for carrying out the automatic focusing operation in the predetermined distance in the vicinity of the analysis end position at which the automatic focusing operation is ended.

4. The analyzer as set forth in claim 1, wherein:

the control means sets, as the predetermined analysis start position, a position to which the objective lens is moved, by means of offset movement of a predetermined distance, from a position where the objective lens is focused on the light-transmitting plate or the light-transmitting covering plate.

5. The analyzer as set forth in claim 1, further comprising:

image pickup means for obtaining an image of the tangible component present in the focus position, if the judgment means judges that the tangible component is present.

6. The analyzer as set forth in claim 5, wherein:

if the judgment means judges that no tangible component is present in the visual field under operation, the image pickup means obtains an image of the sample at the analysis end position at which the automatic focusing operation is ended.

7. The analyzer as set forth in claim 5, further comprising:

classification means for classifying the tangible component in accordance with the image thus obtained.

8. The analyzer as set forth in claim 1, wherein:

the automatic focusing means carries out the automatic focusing operation by using a contrast-based type automatic focusing operation function.

9. An analysis program for operating an analyzer as set forth in claim 1, the analysis program causing a computer to function as each means.

10. A computer-readable storage medium in which an analysis program as set forth in claim 9 is stored.

11. An analysis method for analyzing a tangible component contained in a sample held between a light-transmitting plate and a light-transmitting covering plate, comprising the steps of:

carrying out automatic focusing operation in a range from a predetermined analysis start position to a preset analysis end position, the predetermined analysis start position being between the light-transmitting plate and the light-transmitting covering plate;

judging whether or not a tangible component is present, wherein if a focus state is detected in the step for carrying out the automatic focusing operation, it is judged that a tangible component is present in a focus position at which the focus state is obtained;

if it is judged that the tangible component is present in the judgment step, stopping the automatic focusing operation at the focus position at which the tangible component is judged to be present, and changing, in a horizontal direction, a relative position between the objective lens and the sample so as to carry out another analysis of a tangible component in another visual field; and carrying out, in said another analysis of the tangible component in said another visual field, the automatic focusing operation in a predetermined distance in the vicinity of the focus position at which the tangible component is judged to be present, the predetermined distance being in a vertical direction.

* * * * *